US012668639B2

(12) United States Patent
Yang et al.

(10) Patent No.: US 12,668,639 B2
(45) Date of Patent: Jun. 30, 2026

(54) ANTI-CXCR2 ANTIBODIES AND USES THEREOF

(71) Applicant: ShanghaiTech University, Shanghai (CN)

(72) Inventors: Guang Yang, Shanghai (CN); Xiaojie Shi, Shanghai (CN); Richard Lerner, Shanghai (CN)

(73) Assignee: ShanghaiTech University, Shanghai (CN)

( * ) Notice: Subject to any disclaimer, the term of this patent is extended or adjusted under 35 U.S.C. 154(b) by 1064 days.

(21) Appl. No.: 17/640,309

(22) PCT Filed: Sep. 3, 2020

(86) PCT No.: PCT/CN2020/113197
§ 371 (c)(1),
(2) Date: Mar. 3, 2022

(87) PCT Pub. No.: WO2021/043203
PCT Pub. Date: Mar. 11, 2021

(65) Prior Publication Data
US 2022/0332835 A1      Oct. 20, 2022

(30) Foreign Application Priority Data

Sep. 4, 2019    (WO) ............... PCT/CN2019/104336

(51) Int. Cl.
| | |
|---|---|
| *C07K 16/28* | (2006.01) |
| *A61K 39/00* | (2006.01) |
| *A61P 29/00* | (2006.01) |
| *A61P 35/00* | (2006.01) |
| *G01N 33/68* | (2006.01) |

(52) U.S. Cl.
CPC .......... *C07K 16/2866* (2013.01); *A61P 35/00* (2018.01); *G01N 33/6863* (2013.01); *A61K 2039/505* (2013.01); *C07K 2317/21* (2013.01); *C07K 2317/24* (2013.01); *C07K 2317/34* (2013.01); *C07K 2317/565* (2013.01); *C07K 2317/622* (2013.01); *C07K 2317/76* (2013.01); *C07K 2317/77* (2013.01); *C07K 2317/92* (2013.01); *G01N 2333/521* (2013.01)

(58) Field of Classification Search
CPC ............ C07K 16/2866; C07K 2317/21; C07K 2317/34; C07K 2317/565; C07K 2317/76; C07K 2317/77; C07K 2317/92; C07K 2317/622; C07K 2317/24; A61P 35/00; A61P 29/00; G01N 33/6863; G01N 2333/521; A61K 2039/505
See application file for complete search history.

(56) References Cited

FOREIGN PATENT DOCUMENTS

| | | |
|---|---|---|
| CN | 107964045 A | 4/2018 |
| JP | 2015-524790 | 8/2015 |
| KR | 20140039352 A | 4/2014 |
| WO | WO2012062713 A1 | 5/2012 |
| WO | WO2013168108 A2 | 11/2013 |
| WO | WO2014170317 A1 | 10/2014 |
| WO | WO 2018/154391 | 8/2018 |
| WO | WO2018154391 A1 | 8/2018 |

OTHER PUBLICATIONS

Hall et al. A Single Amino Acid Mutation in CDR3 of the 3-14-9 L Chain abolished expression of the IDA 10-defined Idiotope and Antigen Binding. Journal of immunology (Baltimore, Md. : 1950) (1992). 149 (5):1605-12. (Year: 1992).*

Rabia et al. "Understanding and overcoming trade-offs between antibody affinity, specificity, stability and solubility". Biochem Eng J. Sep. 15, 2018;137:365-374. doi: 10.1016/j.bej.2018.06.003. Epub Jun. 5, 2018. (Year: 2018).*

Vajdos et al. "Comprehensive Functional Maps of the Antigen-binding Site of an Anti-ErbB2 Antibody Obtained with Shotgun Scanning Mutagenesis". J Mol Biol. (2002). 320(2):415-428. (Year: 2002).*

Boppana et al. "Blockade of CXCR2 signalling: A potential therapeutic target for preventing neutrophil-mediated inflammatory diseases". Experimental Biology and Medicine 2014; 239: 509-518. DOI: 10.1177/1535370213520110. (Year: 2014).*

Ha et al. "Role of the CXCL8-CXCR1/2 Axis in Cancer and Inflammatory Diseases". Theranostics. Apr. 7, 2017;7(6):1543-1588. doi: 10.7150/thno.15625. PMID: 28529637; PMCID: PMC5436513. (Year: 2017).*

Rossant, Christine J. et al. "Phage display and hybridoma generation of antibodies to human CXCR2 yields antibodies with distinct mechanisms and epitopes" MAbs 6:6, 2014, 1425-1438.

Rossant Christine J et al. "Phage display and hybridoma generation of antibodies to human CXCR2 yields antibodies with distinct mechanisms and epitopes", MABS, Landes Bioscience, US vol. 6, No. 6, Dec. 1, 2014, pp. 1425-1438.

Ronald S Boshuizen et al. "A combination of in vitro techniques for efficient discovery of functional monoclonal antibodies against human CXC chemokine receptor-2 (CXCR2)" MABS, vol. 6, No. 6, Nov./Dec. 2014, 10 pages.

(Continued)

*Primary Examiner* — Mark Halvorson
*Assistant Examiner* — Lea S O'Brien
(74) *Attorney, Agent, or Firm* — Sheppard Mullin Richter & Hampton LLP

(57) ABSTRACT

Provided are anti-CXCR2 antibodies and antigen-binding fragments thereof. The antibodies or fragments thereof specifically bind to N-terminal, extracellular domain of the CXCR2 protein. In various example, the antibodies or fragments thereof include a VH CDR1 of SEQ ID NO: 1, a VH CDR2 of SEQ ID NO: 2, a VH CDR3 of SEQ ID NO: 3, or any one of SQ ID NO: 7-14, a VL CDR1 of SEQ ID NO: 4, a VL CDR2 of SEQ ID NO: 5, and a VL CDR3 of SEQ ID NO: 6, or variants of each thereof. Methods of using the antibodies or fragments thereof for treating and diagnosing diseases such as cancer and inflammatory diseases are also provided.

12 Claims, 15 Drawing Sheets

Specification includes a Sequence Listing.

(56)  References Cited

OTHER PUBLICATIONS

International Search Report for PCT/CN2020/113197, filed on Sep. 3, 2020, Date of Mailing of International Search Report Dec. 4, 2020, 5 pages.

Tamura, Midori et al. "Structural Correlates of an Anticarcinoma Antibody: Identification of Specificity-Determining Residues (SDRs) and Development of a Minimally Immunogenic Antibody Variant by Retention of SDRs Only" The American Associate of Immunologists, 164 (3): 1432-1441.

Rudikoff, Stuart et al. "Single Amino Acid Subsititution Altering Antigen-Binding Specificity".

Wu et al., "A Chemokine Receptor CXCR2 Macromolecular Complex Regulates Neutrophil Functions in Inflammatory Diseases", 2011, The Journal of Biological Chemistry, vol. 287, No. 8, pp. 5744-5755.

Zhang et al., "The role of CXCR2 in acute inflammatory responses and its antagonists as anti-inflammatory therapeutics", 2019, Curr Opin Hematol., 26(1): 28-33.

Cheng et al., "Potential roles and targeted therapy of the CXCLs/CXCR2 axis in cancer and inflammatory diseases", 2019, BBA—Reviews on Cancer 1871, 289-312.

* cited by examiner

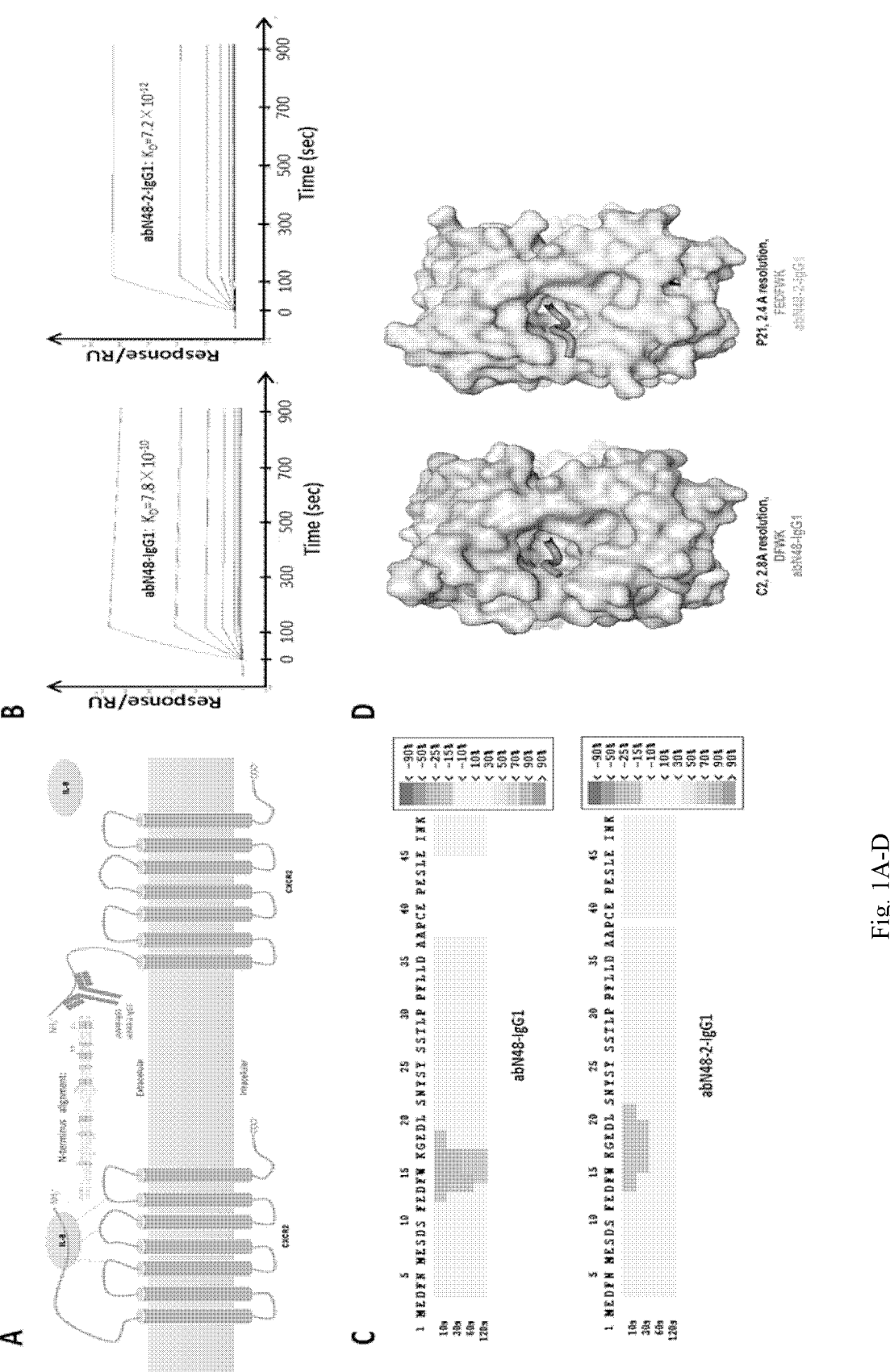
Fig. 1A-D

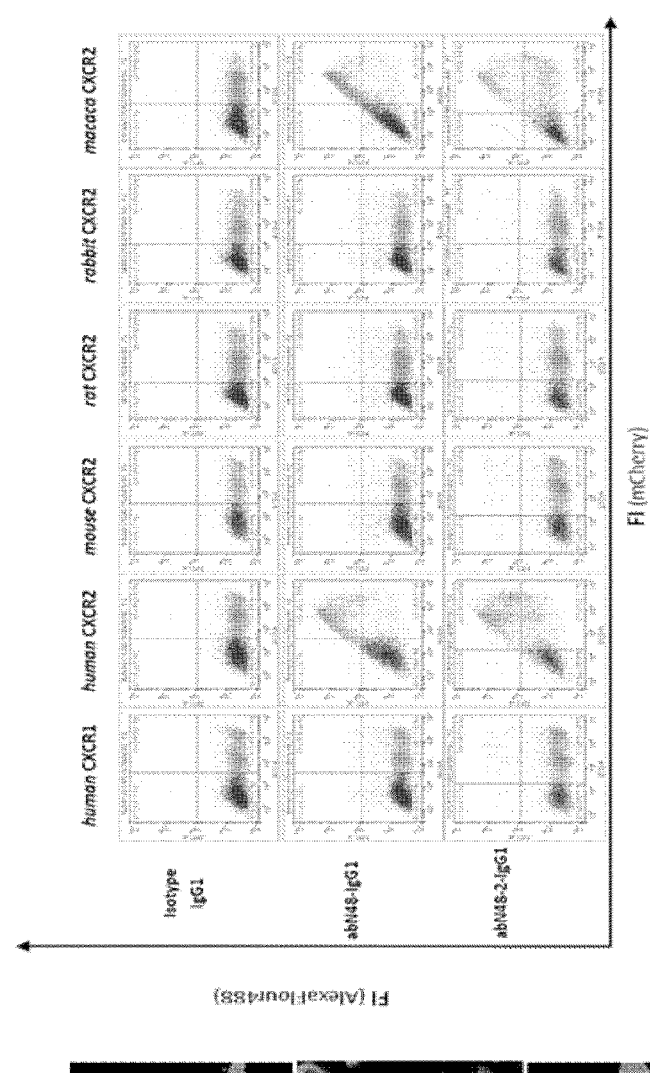
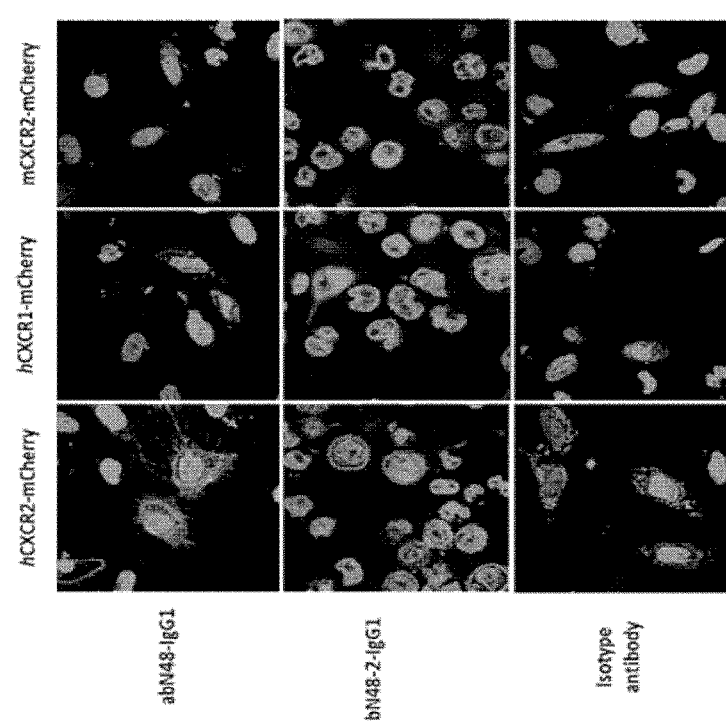
Fig. 2A-B

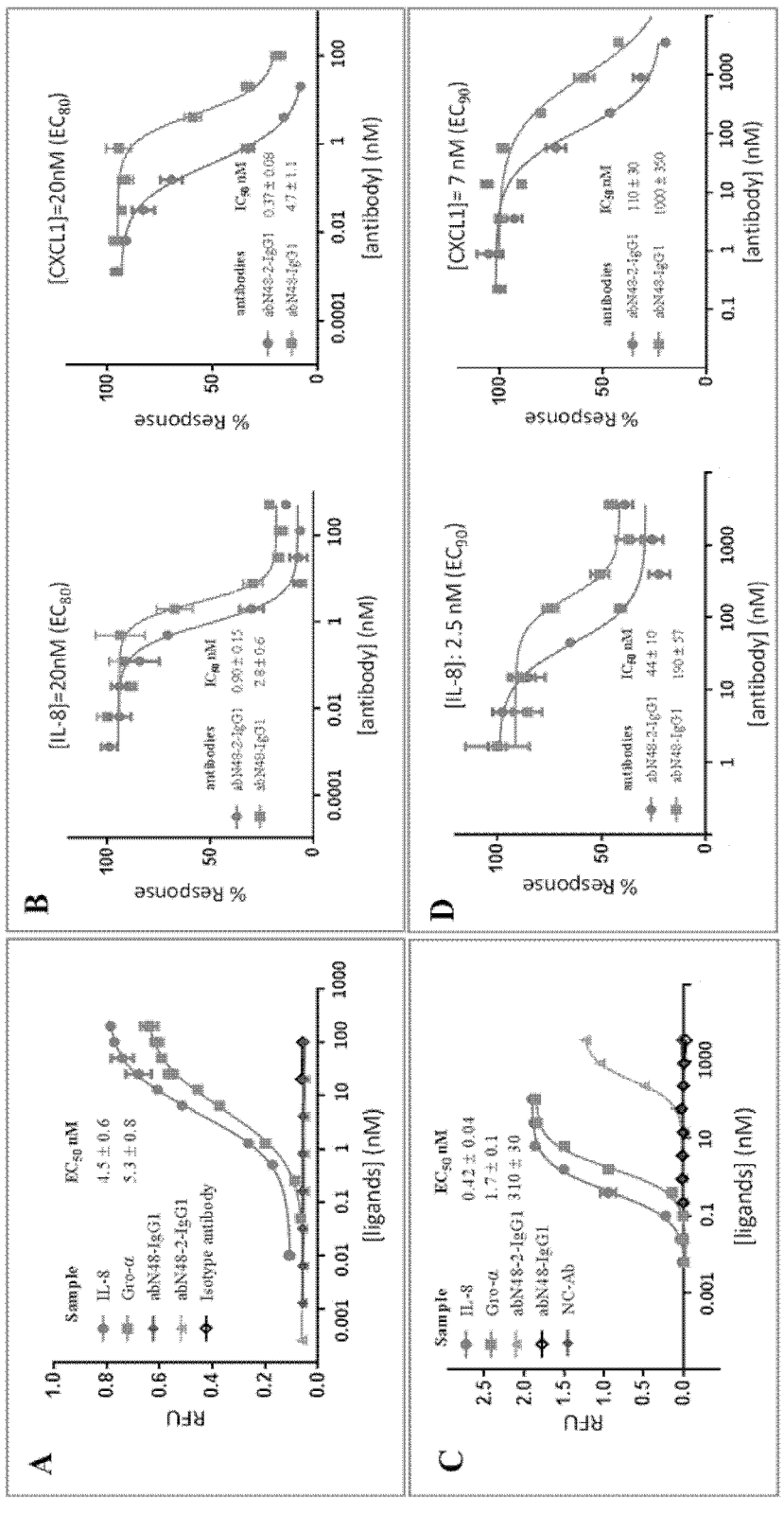
Fig. 3A-D (continuted)

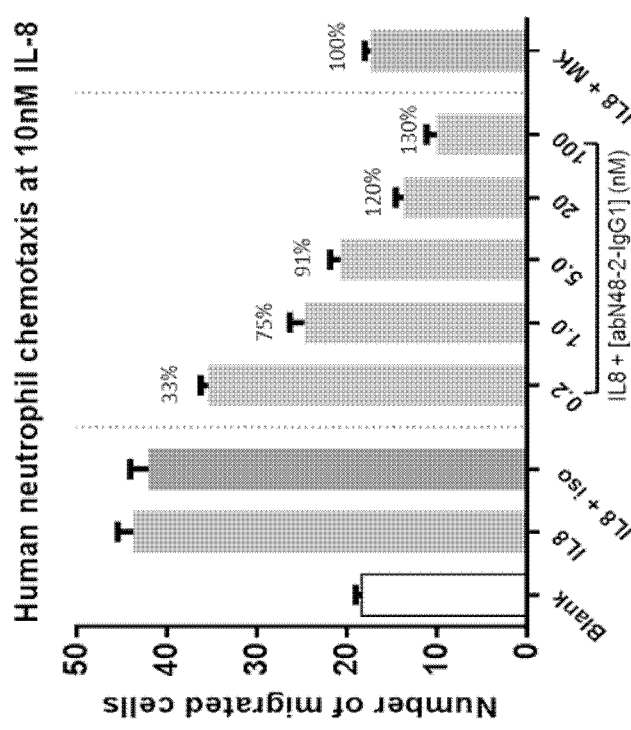
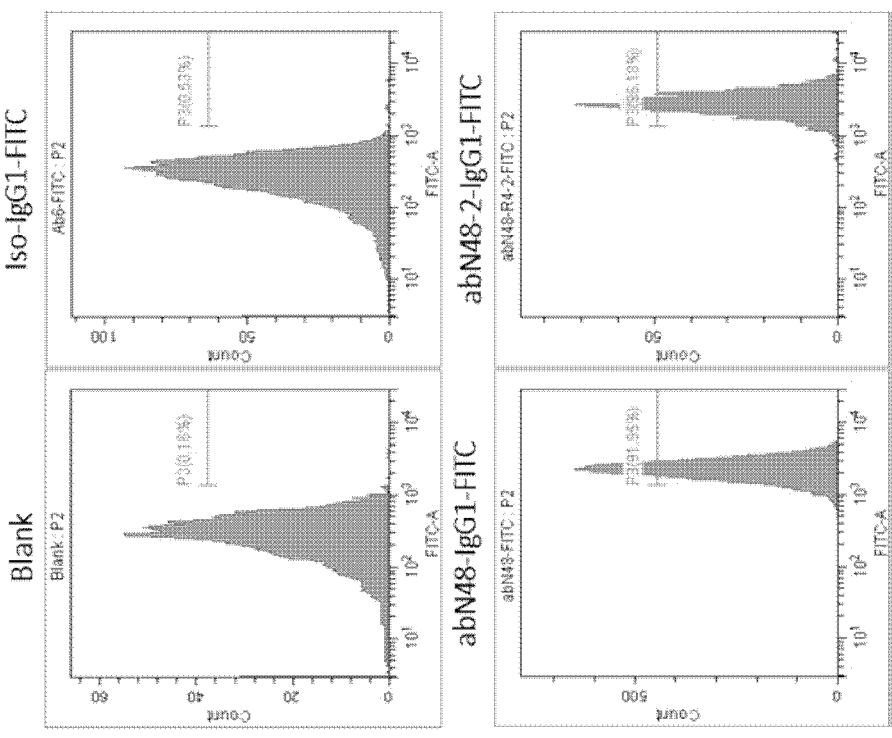
Fig. 4A-B

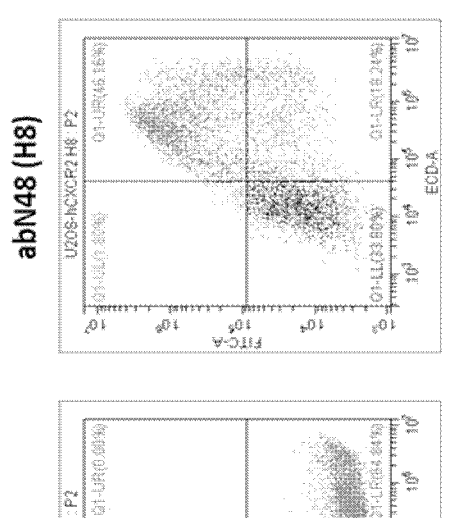
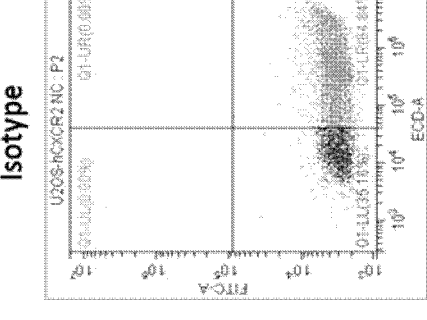
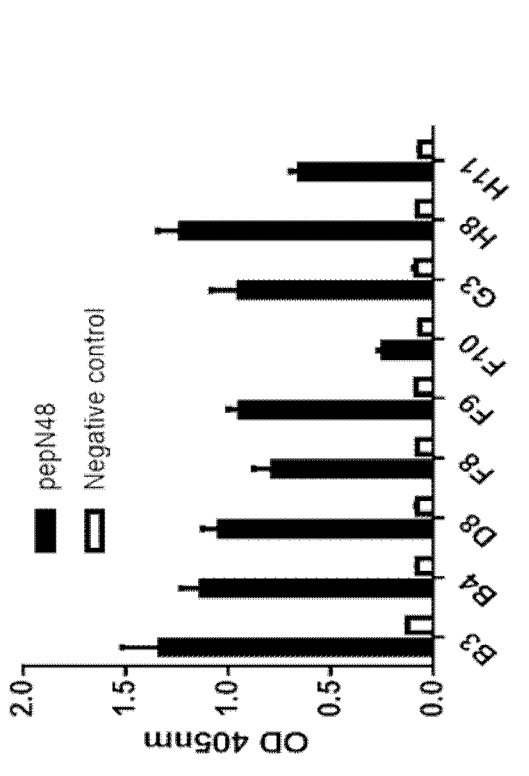
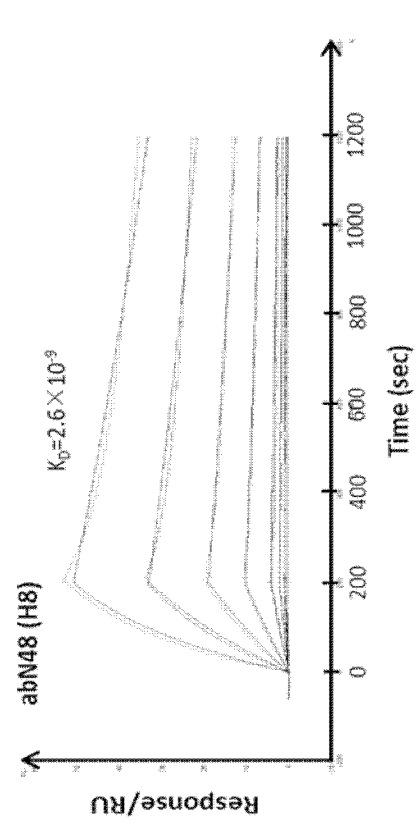
Fig. 5A-C

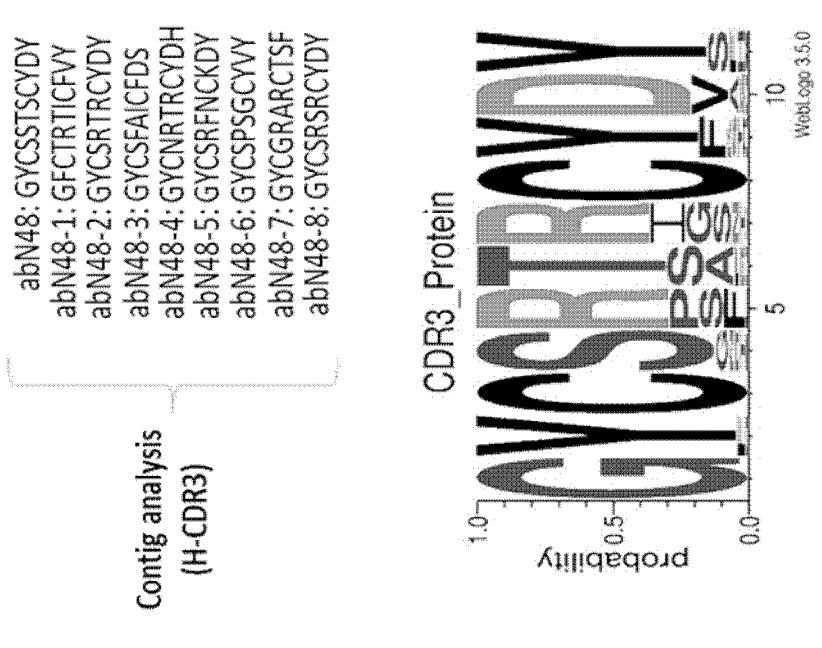
abN48: GYCSSTSCYDY
abN48-1: GFCTRTICFVY
abN48-2: GYCSRTRCYDY
abN48-3: GYCSFAICFDS
abN48-4: GYCNRTRCYDH
abN48-5: GYCSRFNCKDY
abN48-6: GYCSPSGCYVY
abN48-7: GYCGRARCTSF
abN48-8: GYCSRSRCYDY
Contig analysis
(H-CDR3)
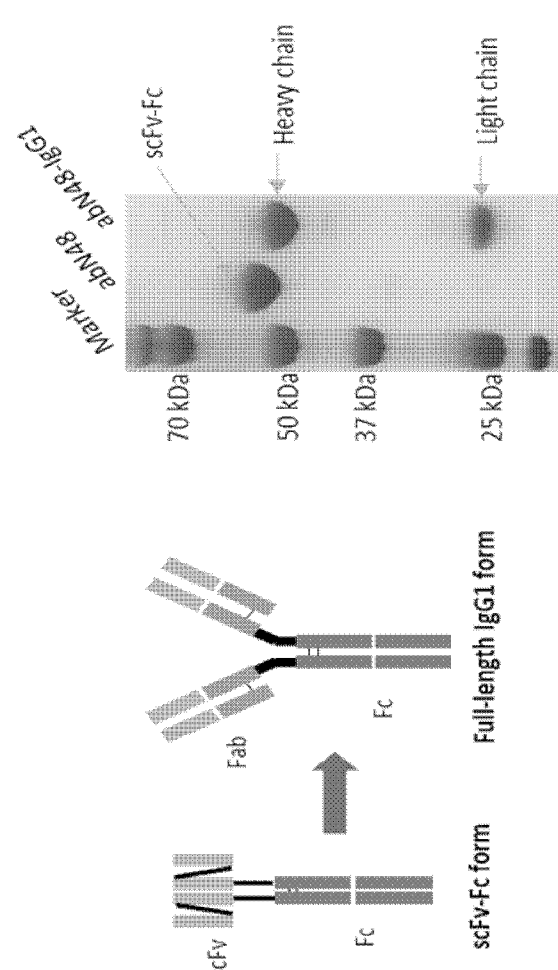
Fig. 6A-B

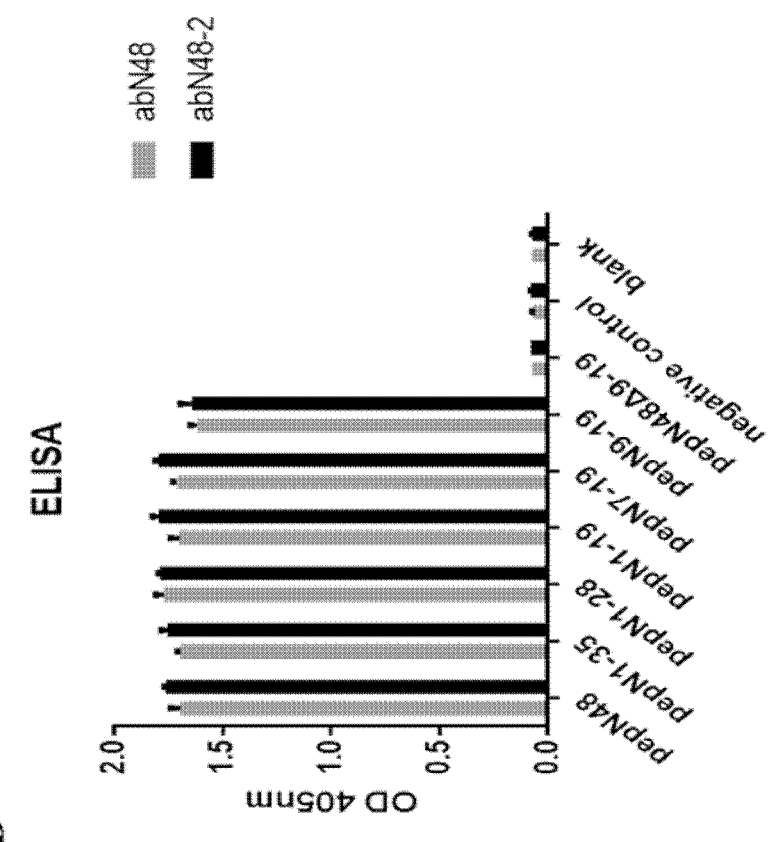
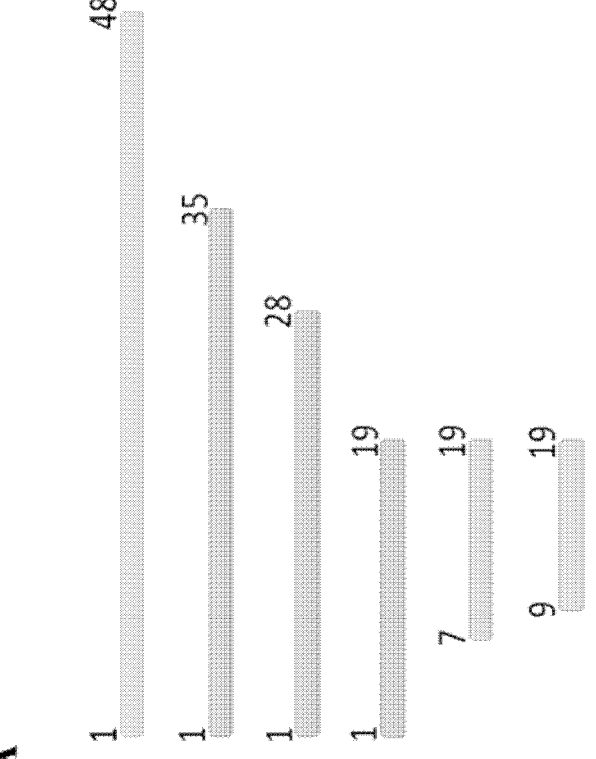
Fig. 9A-B

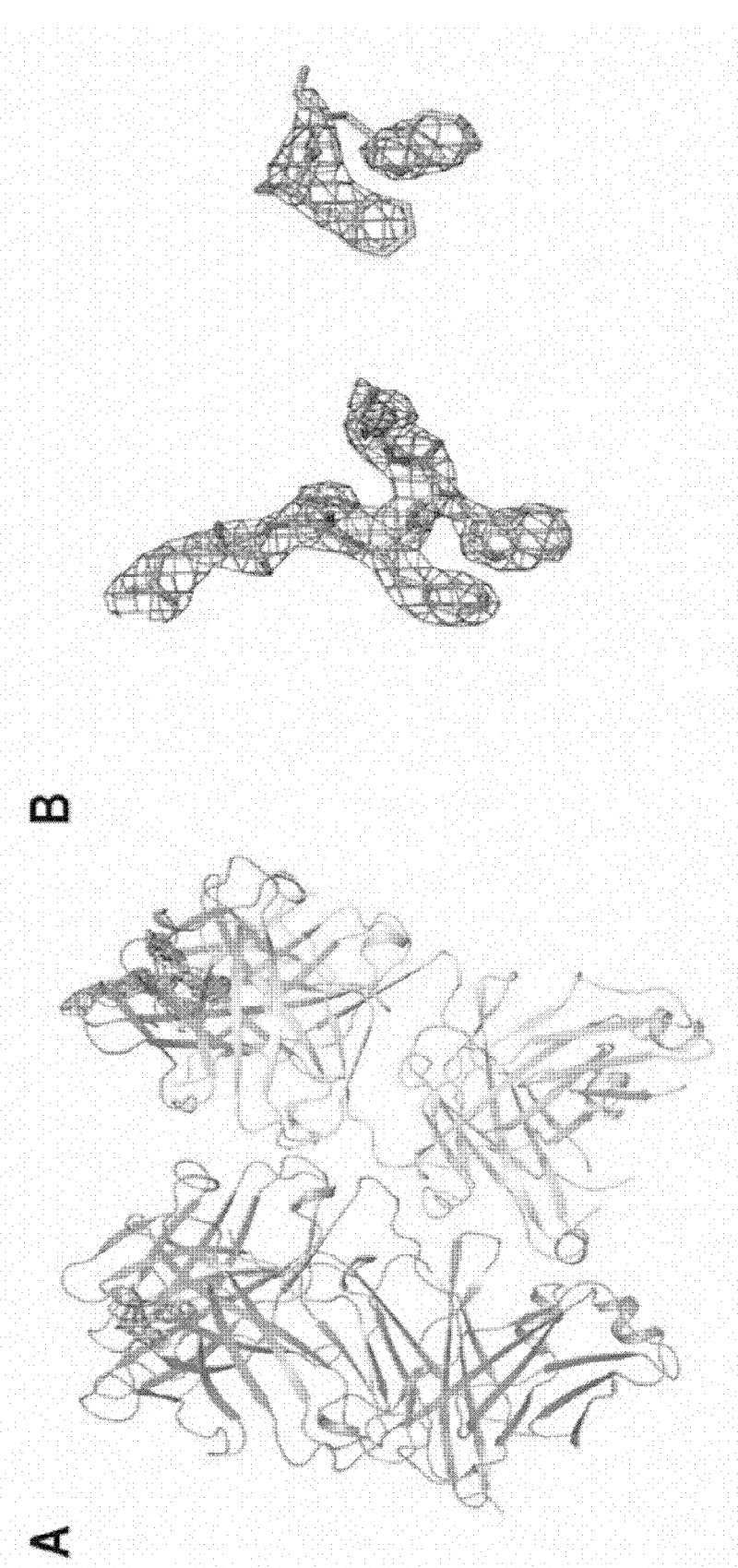
Fig. 10A-B

Fig. 11A-B

A

B

SEQUENCE LISTING

<160> NUMBER OF SEQ ID NOS: 19

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Ser Tyr Ala Ile Ser
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic

<400> SEQUENCE: 2

Trp Ile Asn Pro Asn Ser Gly Gly Thr Asn Tyr Ala Gln Lys Phe Gln
1               5                   10                  15

Gly

-continued

<210> SEQ ID NO 3
<211> LENGTH: 11
<212> TYPE: PRT
<213> ORGANISM: Artificial Sequence
<220> FEATURE:
<223> OTHER INFORMATION: Synthetic

<400> SEQUENCE: 3

Gly Tyr Cys Ser Arg Thr Arg Cys Tyr Asp Tyr
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic

<400> SEQUENCE: 4

Thr Leu Arg Ser Gly Ile Asn Val Gly Ala Tyr Arg Ile Tyr
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Synthetic

<400> SEQUENCE: 5

Tyr Lys Ser Asp Ser Asp Lys Gln Gln Gly Ser
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Ala Ile Trp His Ser Ser Ala Trp Val
1               5

<210> SEQ ID NO 7
<211> LENGTH: 11
<212> TYPE: PRT
<213> ORGANISM: Artificial Sequence
<220> FEATURE:
<223> OTHER INFORMATION: Synthetic

<400> SEQUENCE: 7

Gly Tyr Cys Ser Ser Thr Ser Cys Tyr Asp Tyr
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic

<400> SEQUENCE: 8

Gly Phe Cys Thr Arg Thr Ile Cys Phe Val Tyr
1               5                   10

```
<210> SEQ ID NO 9
<211> LENGTH: 11
<212> TYPE: PRT
<213> ORGANISM: Artificial Sequence
<220> FEATURE:
<223> OTHER INFORMATION: Synthetic

<400> SEQUENCE: 9

Gly Tyr Cys Ser Phe Ala Ile Cys Phe Asp Ser
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic

<400> SEQUENCE: 10

Gly Tyr Cys Asn Arg Thr Arg Cys Tyr Asp His
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Synthetic

<400> SEQUENCE: 11

Gly Tyr Cys Ser Arg Phe Asn Cys Lys Asp Tyr
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic

<400> SEQUENCE: 12

Gly Tyr Cys Ser Pro Ser Gly Cys Tyr Val Tyr
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthetic

<400> SEQUENCE: 13

Gly Tyr Cys Gly Arg Ala Arg Cys Thr Ser Phe
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthetic

<400> SEQUENCE: 14

Gly Tyr Cys Ser Arg Ser Arg Cys Tyr Asp Tyr
1               5                   10

<210> SEQ ID NO 15
```

```
<211> LENGTH: 48
<212> TYPE: PRT
<213> ORGANISM: Artificial Sequence
<220> FEATURE:
<223> OTHER INFORMATION: Synthetic

<400> SEQUENCE: 15

Met Glu Asp Phe Asn Met Glu Ser Asp Ser Phe Glu Asp Phe Trp Lys
1               5                   10                  15

Gly Glu Asp Leu Ser Asn Tyr Ser Tyr Ser Ser Thr Leu Pro Pro Phe
                20                  25                  30

Leu Leu Asp Ala Ala Pro Cys Glu Pro Glu Ser Leu Glu Ile Asn Lys
        35                  40                  45

<210> SEQ ID NO 16
<211> LENGTH: 11
<212> TYPE: PRT
<213> ORGANISM: Artificial Sequence
<220> FEATURE:
<223> OTHER INFORMATION: Synthetic

<400> SEQUENCE: 16

Asp Ser Phe Glu Asp Phe Trp Lys Gly Glu Asp
1               5                   10

<210> SEQ ID NO 17
<211> LENGTH: 120
<212> TYPE: PRT
<213> ORGANISM: Artificial Sequence
<220> FEATURE:
<223> OTHER INFORMATION: Synthetic

<400> SEQUENCE: 17

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Leu Ser Ser Tyr
                20                  25                  30

Ala Ile Ser Trp Val Arg Gln Ala Pro Gly Gln Gly Pro Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Pro Asp Asp Thr Ala Val Tyr Tyr Cys
                85                  90                  95

Ala Ser Gly Tyr Cys Ser Ser Thr Ser Cys Tyr Asp Tyr Trp Gly Gln
                100                 105                 110

Gly Thr Leu Val Thr Val Ser Ser
        115                 120

<210> SEQ ID NO 18
<211> LENGTH: 120
<212> TYPE: PRT
<213> ORGANISM: Artificial Sequence
<220> FEATURE:
<223> OTHER INFORMATION: Synthetic

<400> SEQUENCE: 18

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Leu Ser Ser Tyr
                20                  25                  30
```

-continued

```
Ala Ile Ser Trp Val Arg Gln Ala Pro Gly Gln Gly Pro Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Pro Asp Asp Thr Ala Val Tyr Tyr Cys
                85                  90                  95

Ala Ser Gly Tyr Cys Ser Arg Thr Arg Cys Tyr Asp Tyr Trp Gly Gln
            100                 105                 110

Gly Thr Leu Val Thr Val Ser Ser
        115                 120

<210> SEQ ID NO 19
<211> LENGTH: 116
<212> TYPE: PRT
<213> ORGANISM: Artificial Sequence
<220> FEATURE:
<223> OTHER INFORMATION: Synthetic

<400> SEQUENCE: 19

Gln Ala Val Leu Thr Gln Pro Ser Ser Leu Ser Ala Ser Pro Gly Ala
1               5                   10                  15

Ser Val Ser Leu Thr Cys Thr Leu Arg Ser Gly Ile Asn Val Gly Ala
            20                  25                  30

Tyr Arg Ile Tyr Trp Tyr Gln Gln Lys Pro Gly Ser Pro Pro Gln Phe
        35                  40                  45

Leu Leu Arg Tyr Lys Ser Asp Ser Asp Lys Gln Gln Gly Ser Gly Val
    50                  55                  60

Pro Ser Arg Phe Ser Gly Ser Arg Asp Ala Ser Ala Asn Ala Gly Ile
65                  70                  75                  80

Leu Leu Ile Ser Gly Leu Arg Ser Glu Asp Glu Ala Asp Tyr Tyr Cys
                85                  90                  95

Ala Ile Trp His Ser Ser Ala Trp Val Phe Gly Gly Gly Thr Gln Leu
            100                 105                 110

Thr Val Leu Gly
        115
```

ANTI-CXCR2 ANTIBODIES AND USES THEREOF

CROSS REFERENCE TO RELATED APPLICATIONS

This application is a U.S. National Stage Application under 35 U.S.C. 371 of International Application No. PCT/CN2020/113197, filed Sep. 3, 2020, which claims priority to Application No. PCT/CN2019/104336, filed Sep. 4, 2019, the content of which is incorporated by reference in its entirety into the present disclosure.

SEQUENCE LISTING

The instant application contains a Sequence Listing which has been submitted electronically in ASCII format and is hereby incorporated by reference in its entirety. Said ASCII copy, created on Mar. 3, 2022, is named 298538US_ST25 and is 7 KB in size.

BACKGROUND

The G protein coupled-receptor (GPCR) superfamily is one of the largest families in the human genome, consisting of over eight hundred members, with a broad spectrum of distribution in various organs and tissues, including the central nervous, immune, and cardiovascular systems. GPCRs are widely involved in a range of physiological and pathological processes in humans. Almost 40% of approved drugs mediate their effects through GPCRs.

Based on evolutionary homology and properties of their physiological ligands, most GPCR proteins can be grouped into one of five main families: Rhodopsin, Adhesion, Secretin, Glutamate and Frizzled/TAS2. Rhodopsin is the largest and most heterogeneous family, and can be further divided into four sub-families, $\alpha$, $\beta$, $\gamma$, and $\delta$. These proteins have a similar structure: an extracellular N-terminus, seven transmembrane regions, and a cytoplasmic C-terminus. They sense various extracellular stimuli through interactions with a variety of ligands, such as amino acids, nucleic acids, peptides and proteins, and activate intracellular signaling pathways via ligand-induced conformational changes. In canonical signaling, GPCR signals are transduced through recruitment of intracellular GTP-dependent proteins (G proteins) onto specific cytoplasmic regions of the C-terminus—the so-called G protein-dependent signaling. Following this, depending on the particular G protein involved, downstream pathways including cAMP or the PIP2 pathway are activated.

Moreover, recruitment of other intracellular scaffold proteins, e.g., $\beta$-arrestins, has been shown to activate G protein-independent signaling events. Multiplex signaling endows GPCRs with parallel functions in a cell, and makes it difficult to design relevant assays linking any single target receptor to specific downstream cellular activities. It remains a challenge for the pharmaceutical industry to develop highly effective therapeutics against these important targets. In addition, while antibodies have emerged as an ever increasing source of new therapies, as yet only one therapeutic antibody to GPCRs has been developed, largely because it is difficult to generate antibodies that bind to functional conformations of these membrane proteins.

Combinatorial antibodies have emerged as a powerful tool in drug discovery. Over 80 antibodies yielded from phage panning have entered clinical studies and more than 10 of them have been granted marketing approvals. The combinatorial antibody library approach takes advantage of the vast diversity of a repertoire consisting of up to 1014 distinct binding molecules. Antibodies selected from such libraries have shown diverse mechanisms, and can be neutralizing or function as an agonist, antagonist, or inverse agonist. In some cases they have been shown to function beyond the scope of native ligands.

CXCR2 (C—X—C Motif Chemokine Receptor 2), a member of the chemokine receptor family, is mainly expressed on neutrophils. CXCR2 has been shown to be involved in the neutrophil chemotaxis which normally follows inflammatory stimuli. However, unwanted migration of neutrophils can be a large part of the pathophysiology in a wide variety of diseases associated with inflammation, including colitis, chronic obstructive pulmonary disease (COPD), asthma, and glomerulonephritis. For example, a previous study has reported that depletion of CXCR2 protects lungs from cigarette smoke-induced inflammation and injury. In addition, CXCR2 has been shown to participate in the progression of different types of cancer, playing a significant role in proliferation, survival, and metastasis of tumor cells, and affecting the whole tumor microenvironment.

Given these clinical findings, inhibition of CXCR2-induced neutrophil migration has been seen as an important, but as yet unrealized, strategy to treat neutrophil-related inflammatory diseases and some cancers. Several small molecules targeting CXCR2 have already shown remarkable inhibitory effect on the receptor in vitro or in animal studies, but they have not shown therapeutic efficacy in the clinical setting. This is thought to be due to non-functional binding to CXCR2 and off-target effects.

In contrast, antibodies could overcome these clinical difficulties in that they have high specificity, high serum stability, high safety and, because of their size, block ligand binding to the receptors. However, because of the difficulty in preparing adequate quantities of stable antigen in native conformation for selection, it has been challenging to identify functional antibodies targeting GPCRs.

SUMMARY

The present disclosure provides antibodies and antigen-binding fragments capable of binding to CXCR2 and effectively inhibiting or even completely blocking its binding by IL-8, thereby inhibiting IL8-induced neutrophil chemotaxis. These antibodies and fragments exhibited superior affinity (e.g., at picomolar level) which can overcome the problem that IL8 itself binds with high affinity (nano-molar), leading to a total inhibition of IL8 induced cellular functions. Moreover, these antibodies displayed a biased agonism effect and activated endocytosis of CXCR2, which could lead to more efficient inhibition of CXCR2-mediated pathological events.

Further experiments show that the tested anti-CXCR2 antibodies interact with CXCR2 primarily through the side chains of some of the amino acid residues in the extracellular N-terminus (residues 1-48, in particular residues 9-19) of the human CXCR2 protein. That such interactions were sufficient to inhibit IL8 binding and IL8 induced cellular functions is surprising and unexpected, at least because it was earlier suggested that CXCR2 has three other extracellular domains (loops) which are also involved in IL8 binding.

In accordance with one embodiment of the present disclosure, therefore, provided is an antibody or fragment thereof, wherein the antibody or fragment thereof can specifically bind to a human C—X—C Motif Chemokine Receptor 2 (CXCR2) protein, wherein the binding involves at least one of amino acid residues within residues 9-19 of SEQ ID NO:15. In some embodiments, the binding involves at least one of D13, F14 and W15. In some embodiments, the binding involves at least F14 and W15. In some embodiments, the binding involves at least D13, F14 and W15. In some embodiments, the binding does not involve any amino acid residue outside the 48 N-terminal residues. In some embodiments, the antibody or fragment thereof inhibits binding between the CXCR2 and an IL-8 protein.

Another embodiment provides an antibody or fragment thereof, wherein the antibody or fragment thereof has specificity to a human C—X—C Motif Chemokine Receptor 2 (CXCR2) protein and comprises a heavy chain variable region (VH) comprising a CDR1, a CDR2 and a CDR3, and a light chain variable region (VL) comprising a CDR1, a CDR2 and a CDR3, wherein the VH CDR1 comprises the amino acid sequence of SEQ ID NO:1, or a variant having an amino acid substitution from SEQ ID NO:1; the VH CDR2 comprises the amino acid sequence of SEQ ID NO:2, or a variant having an amino acid substitution from SEQ ID NO:2; the VH CDR3 comprises the amino acid sequence of SEQ ID NO:3, a variant having an amino acid substitution from SEQ ID NO:3, or a variant selected from the group consisting of SEQ ID NO:7-14; the VL CDR1 comprises the amino acid sequence of SEQ ID NO:4, or a variant having an amino acid substitution from SEQ ID NO:4; the VL CDR2 comprises the amino acid sequence of SEQ ID NO:5, or a variant having an amino acid substitution from SEQ ID NO:5; and the VL CDR3 comprises the amino acid sequence of SEQ ID NO:6, or a variant having an amino acid substitution from SEQ ID NO:6.

In some embodiments, the VH CDR1 comprises the amino acid sequence of SEQ ID NO:1; the VH CDR2 comprises the amino acid sequence of SEQ ID NO:2; the VH CDR3 comprises the amino acid sequence of SEQ ID NO:3, or a variant selected from the group consisting of SEQ ID NO:7-14; the VL CDR1 comprises the amino acid sequence of SEQ ID NO:4; the VL CDR2 comprises the amino acid sequence of SEQ ID NO:5; and the VL CDR3 comprises the amino acid sequence of SEQ ID NO:6. In some embodiments, the VH CDR3 comprises the amino acid sequence of SEQ ID NO:3.

In some embodiments, the VH comprises the amino acid sequence of SEQ ID NO:17 or 18, or a peptide having at least 90% sequence identity to SEQ ID NO:17 or 18. In some embodiments, the VH comprises the amino acid sequence of SEQ ID NO:18, or a peptide having at least 90% sequence identity to SEQ ID NO:18. In some embodiments, the VL comprises the amino acid sequence of SEQ ID NO:19, or a peptide having at least 90% sequence identity to SEQ ID NO:19.

Treatment methods and uses are also provided. In one embodiment, a method of treating cancer or an inflammatory disease in a patient in need thereof is provided, comprising administering to the patient an effective amount of the antibody or fragment thereof of the present disclosure. In some embodiments, the cancer is a solid tumor. In some embodiments, the cancer is selected from the group consisting of bladder cancer, liver cancer, colon cancer, rectal cancer, endometrial cancer, leukemia, lymphoma, pancreatic cancer, small cell lung cancer, non-small cell lung cancer, breast cancer, urethral cancer, head and neck cancer, gastrointestinal cancer, stomach cancer, esophageal cancer, ovarian cancer, renal cancer, melanoma, prostate cancer and thyroid cancer.

In some embodiments, the inflammatory disease is one or more of Parkinson's disease, arthritis, rheumatoid arthritis, multiple sclerosis, psoriasis, psoriatic arthritis, Crohn's disease, inflammatory bowel disease, ulcerative colitis, lupus, systemic lupus erythematous, juvenile rheumatoid arthritis, juvenile idiopathic arthritis, Grave's disease, Hashimoto's thyroiditis, Addison's disease, celiac disease, dermatomyositis, multiple sclerosis, myasthenia gravis, pernicious anemia, Sjogren syndrome, type I diabetes, vasculitis, uveitis, atherosclerosis and ankylosing spondylitis.

BRIEF DESCRIPTION OF THE DRAWINGS

FIG. 1A-D. Epitope-guided selection of tight binding antibodies for hCXCR2. (A) Schematic illustration of antibodies selected by phage panning based on IL-8 epitope on the extracellular N-terminus of human CXCR2; (B) Binding affinity measurement of two combinatorial antibodies, abN48-IgG1 and abN48-2-IgG1 by SPR (fitted curves in sensorgram plot & KD value); (C) HDX-MS results showing the binding sites of the selected antibodies to N-terminus of CXCR2; (D) Crystal structures resolved showing the 3D structure of abN48-IgG1 and abN48-2-IgG1 (grey and purple, respectively) complexed with the epitope sequence of human CXCR2 N-terminus (green and red lines).

FIG. 2A-B. Species and subtype specificities of abN48-IgG1 and ab48-2-IgG1. (A) Co-localization of abN48-IgG1 or abN48-2-IgG1 to hCXCR2, hCXCR1, and mCXCR2 overexpressed on the membrane of U20S cells. All the testing receptor proteins were fused with a mCherry fluorescent tag, and the immunocytofluorescent images were captured by confocal microscopy; (B) Surface interactions of abN48-IgG1 and abN48-2-IgG1 with hCXCR2, hCXCR1, mCXCR2, rCXCR2, rabbitCXCR2 and macacaCXCR2 overexpressed on U2OS cells.

Flow-cytometry was used to measure the interactions between antibodies and the CXCR2 receptor proteins.

FIG. 3A-E. CXCR2 mediated cellular signaling pathways. (A) Activation of β-arrestin signaling by IL-8, GROα (CXCL1), and the abN48 antibody ligands using Tango reporter gene assay; (B) Inhibition of chemokine induced β-arrestin signaling by abN48-IgG1 and abN48-2-IgG1. Induction concentration of IL-8 (left) and CXCL1 (right) were at their corresponding EC80 values; (C) Activation of Ca2+influx by IL-8, GROα (CXCL1), and the abN48 antibody ligands using FLIPR measurement; (D) Inhibition of chemokine induced Ca2+influx by abN48-IgG1 and abN48-2-IgG1. Induction concentration of IL-8 (left) and CXCL1 (right) were at their corresponding EC90 values. Data are represented as mean±standard deviation. The calculated EC50 and IC50 values are listed next to the fitted curves. (E) Activation of CXCR2 internalization by abN48 antibodies. U20S cell with or without CXCR2 stable overexpression were used for immunotoxin complex of abN48-IgG1 and toxin, antibody or toxin only. Data are represented as mean±standard deviation.

FIG. 4A-B. abN48-IgG1 and abN48-2-IgG1 potently inhibit IL-8 induced neutrophil chemotaxis (A) abN48-IgG1 and abN48-2-IgG1 (FITC-conjugated) specifically bind to human primary neutrophils at same level. (B) Inhibition effect of abN48-IgG1 and abN48-2-IgG1 on 1L8 (10 nM) induced neutrophil chemotaxis was determined by Chemotaxis Assay. Blank: media without IL8 or inhibitor, IL8: 10 nM IL8, iso: 10 nM irrelevant human IgG1 antibody, MK: 1 μM small molecule CXCR2 inhibitor MK7123. The values of percentage (%) above the blue and green bars represent the percentage of inhibition of neutrophil chemotaxis induced by IL8 at various concentrations of abN48-2-IgG2 and 1 μM MK7123, respectively.

FIG. 5A-C. Selection of combinatorial antibody targeting hCXCR2. (A) Nine positive clones from library panning was expressed as secreted combinatorial scFv antibodies, in which H8 is also represented as abN48. Binding of these clones with pepN48 was confirmed by ELISA. (B) Binding of abN48 (H8) to hCXCR2 expressed on cell surface was measured by FACS. (C) Binding affinity of abN48 (H8) with pepN48 was determined by SPR assay on a Biacore T200.

FIG. 6A-B. Full-length abN48-IgG1 purification and mutant CDR3 sequences alignment. (A) Illustration of full-length IgG1 format antibody construction from abN48 to abN48-IgG, and SDS-PAGE of abN48 and abN48-IgG1. (B) Weblogo analysis of mutant CDR3 sequences in affinity maturation.

Figure 7:
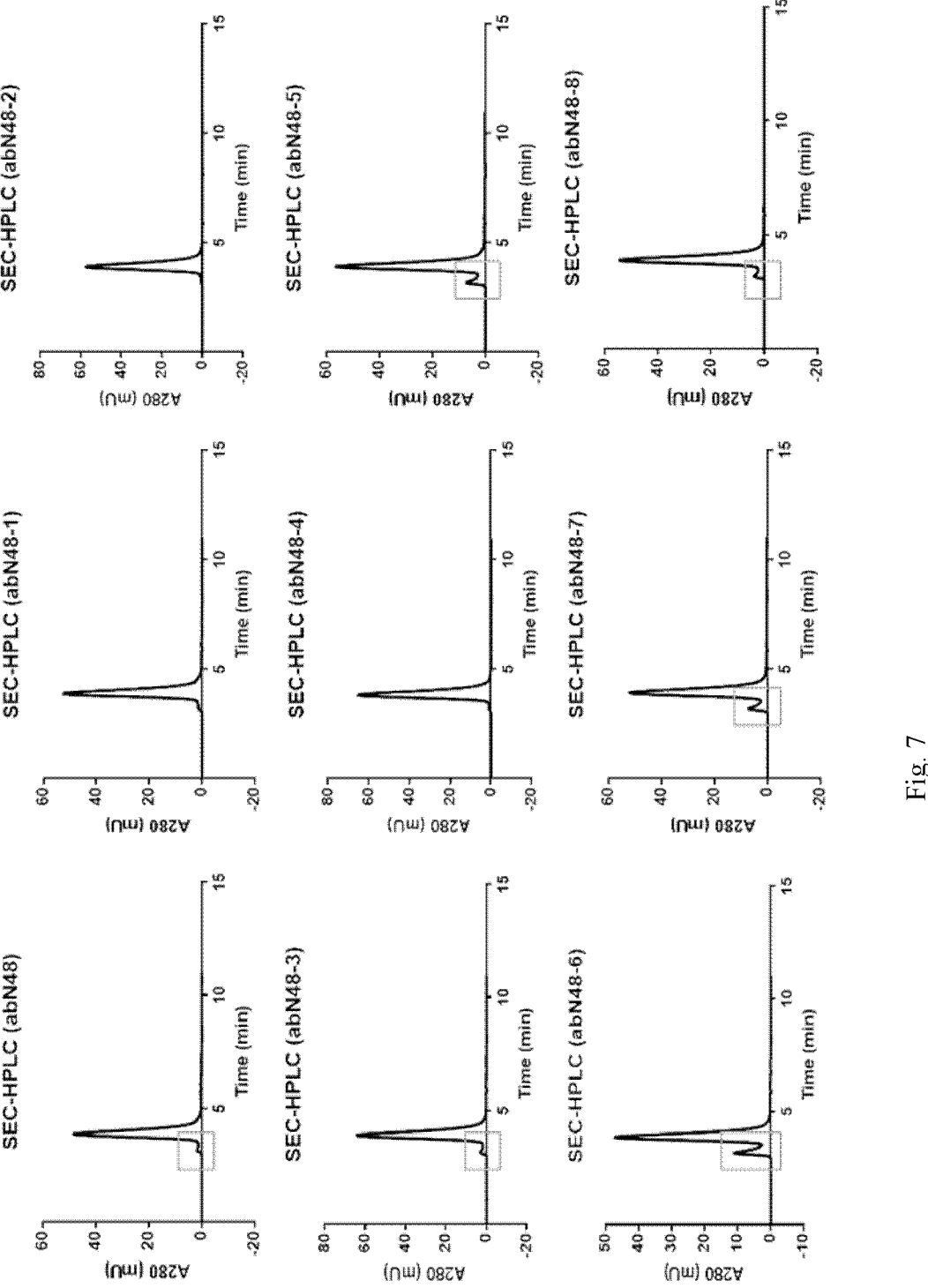

FIG. 7. Homogeneity analyses of recombinant combinatorial antibodies by SEC-HPLC. The shoulder peaks highlighted in red rectangular frames represent impurities generated during the incubation of antibody protein at 42° C.

Figure 8:
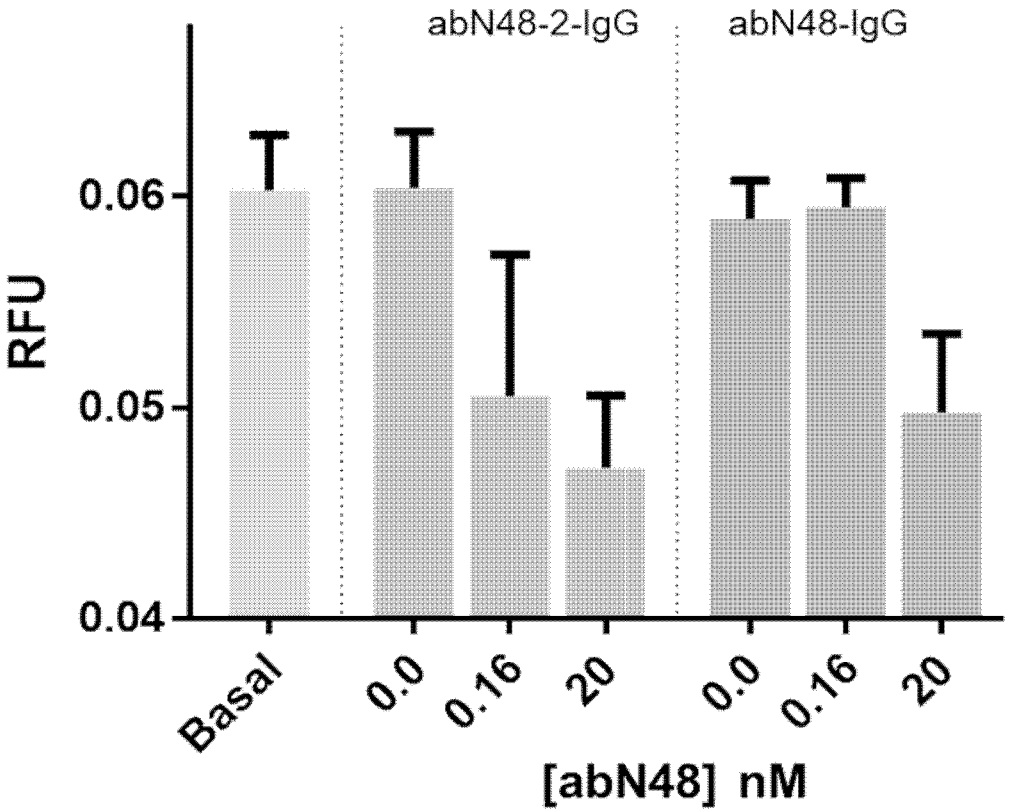

FIG. 8. Inverse agonist effect of combinatorial antibody on CXCR2 mediated β-arrestin signaling. The intrinsic β-arrestin recruitment (represented as red bar labed as Basal) induced by the membrane expression of hCXCR2 was significantly reduced in the presence of different concentrations of abN48-IgG1 (green bars) and abN48-2-IgG1 (blue bars).

FIG. 9A-B. Truncation mutagenesis of N-terminus of hCXCR2 for mapping the epitope region. (A) Schematic illustration of designed N- or C-terminal truncated synthetic peptides of CXCR2-N-terminu; (B) Interactions between N-terminal peptides of hCXCR2 and abN48-IgG1 (grey) or abN48-2-IgG1 (black).

FIG. 10A-B. Overall Structure of abN48/NT9-19 protein complex. (A) Two abN48 in one asymmetric unit were shown as cartoon models, and bound NT9-19 peptides were depicted as yellow stick models surrounded by 2Fo-Fc electron density map contoured at 1.1σ. The left abN48 was colored grey and the other was colored as following: light chain, cyan; heavy chain, tint; light chain CDRs, tv_green; heavy chain CDRs, tv_red. (B) In one abN48/NT9-19 protein complex, residues EDFWK12-16aa of NT9-19 could be well traced from the electron density (left) while in the other, only the electron density for residues FW14-15aa could be seen (right). The residues that could be traced from the electron density were depicted as yellow stick models surrounded by marine (left) or purple (right) density maps contoured at 1.1 σ.

Figure 11C:
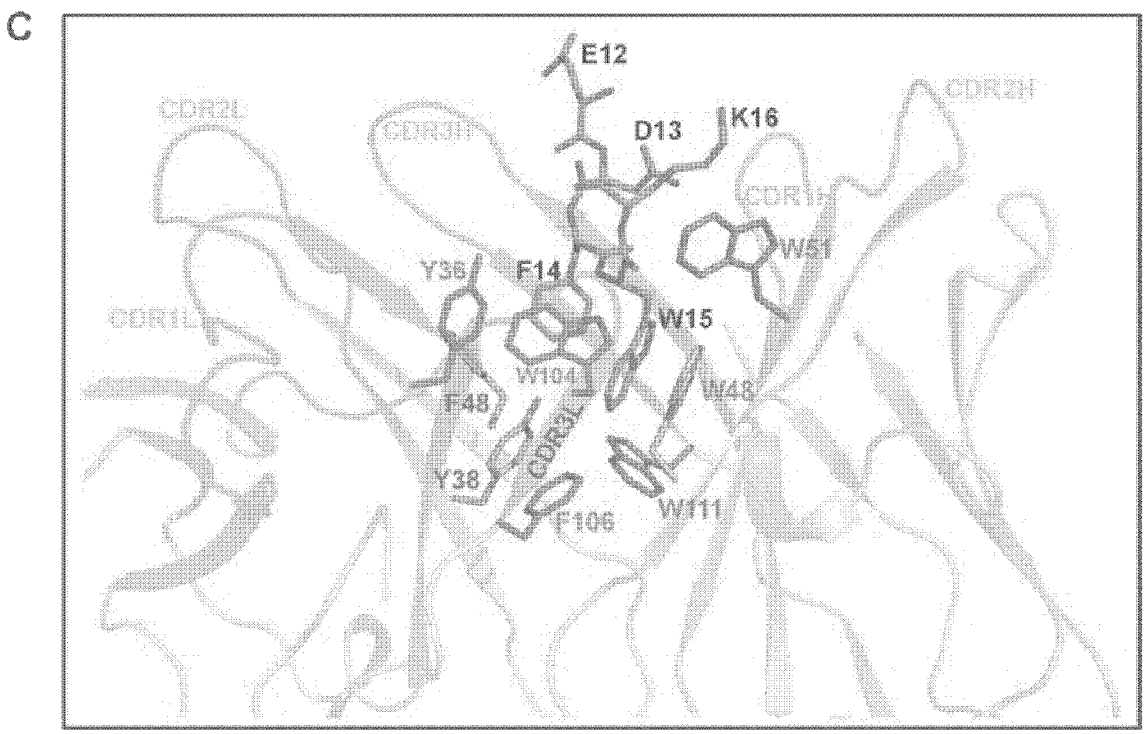

FIG. 11A-C. Residues EDFWK12-16aa of CXCR2_N interact with the CDR loops of abN48 mainly through hydrophobic interactions. (A) Side-view structure (left) and top-view structure (right) of abN48 in complex with NT9-19. The CDR loops of the heavy chain is colored tv_red and that of the light chain is colored tv_green, the rest of abN48 light chain is colored cyan and the rest of abN48 heavy chain is colored tint. Residues EDFWK12-16aa of NT9-19 could be traced from the electron density and are shown as a yellow stick model surrounded by 2Fo-Fc electron density map contoured at 1.1σ. Except for the CDR loops, the rest of abN48 were rendered transparent for clarity. (B) Residues FW14-15aa of NT9-19 snugly fit themselves into a large hydrophobic pocket formed by CDR loops at the top of abN48. Electrostatic surface drawings of abN48 is colored according to the local electrostatic potential, which ranges from +10 V (dark blue) to −10 V (dark red). (C) F14 and W15 of NT9-19 insert their bulky aromatic side chains into the hydrophobic cavity formed by the CDR loops of abN48, mainly forming strong 7-7L stacking interaction with residues from abN48. Residues EDFWK12-16aa of NT9-19 and related residues on abN48 were all depicted as stick models and colored coded as in (A).

Figure 12A:
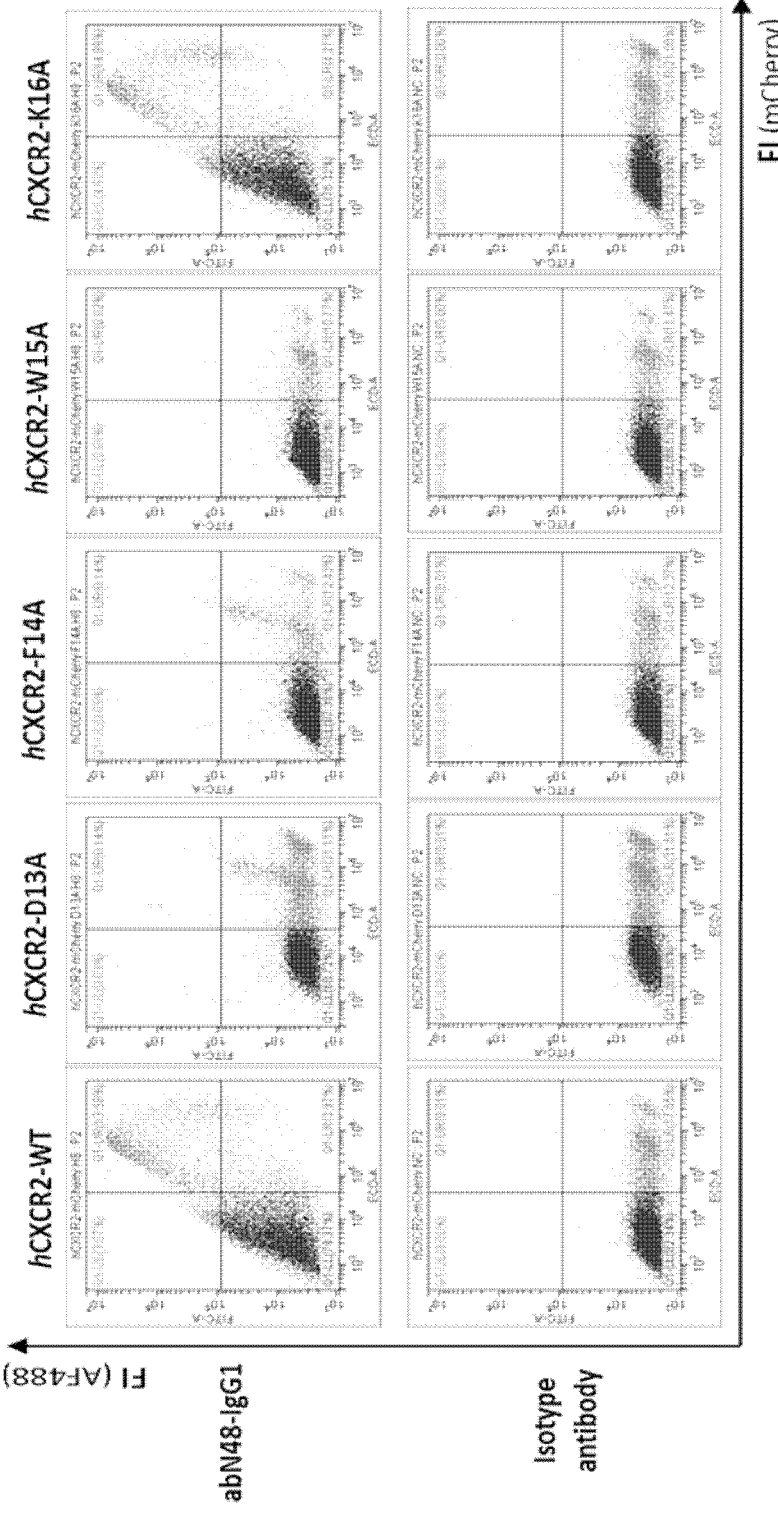
Figure 12B:
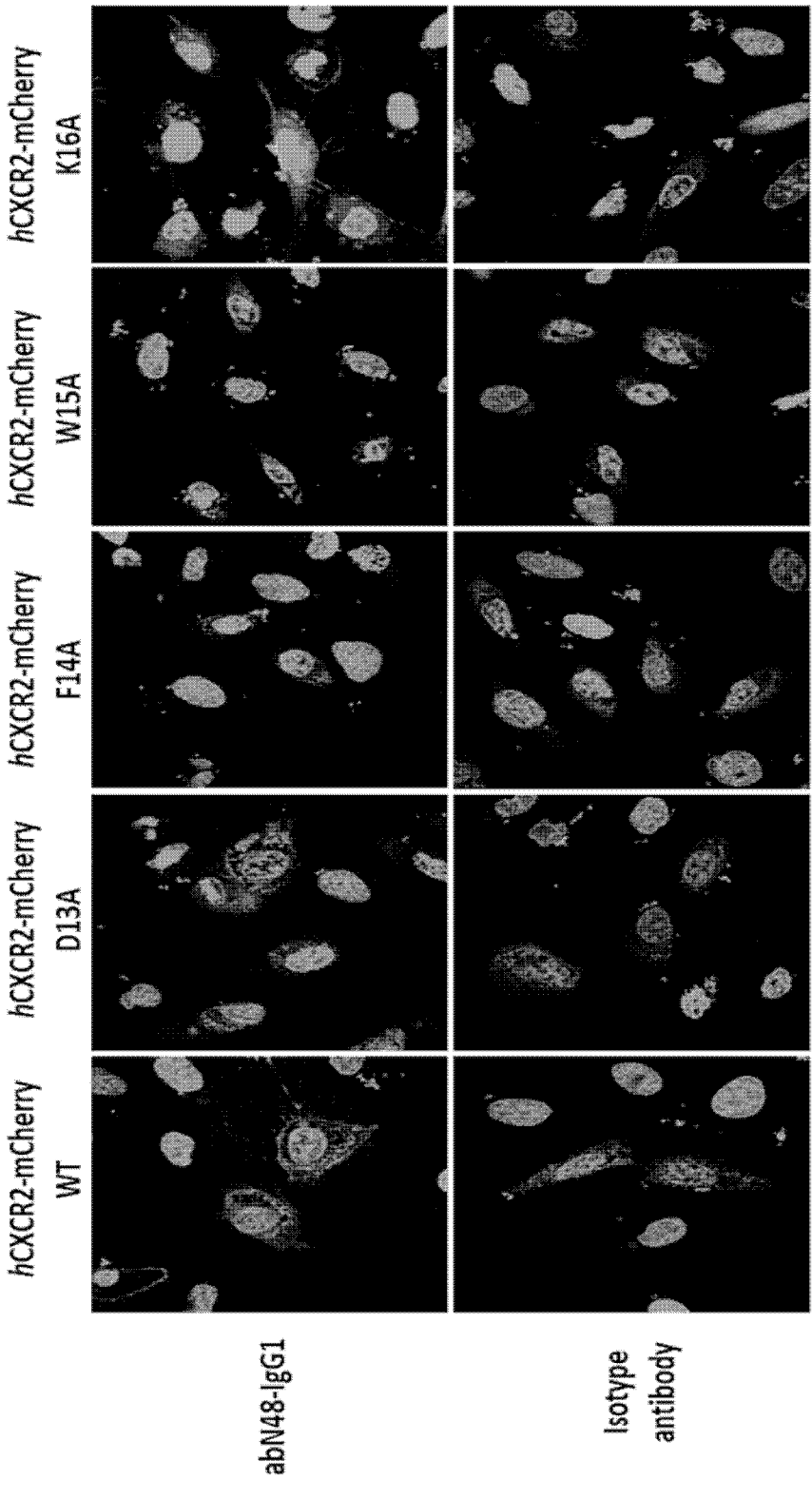

FIG. 12A-B. Site-directed mutagenesis for epitope mapping. The Amino acid residues in the IL-8 binding region on hCXCR2 N-terminus (D13, F14, W15, K16) were subjected to alanine-scan site-directed mutagenesis. The point mutants of hCXCR2 were ectopically expressed on U2OS cells as mCherry fusion proteins, and stained by the abN48-IgG1 antibody. (A) ICC; and (B) FACS results all showed that D13, F14 and W15 are the three key residues for antibody binding.

DETAILED DESCRIPTION

Definitions

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present disclosure.

The term "an equivalent nucleic acid or polynucleotide" refers to a nucleic acid having a nucleotide sequence having a certain degree of homology, or sequence identity, with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof. Likewise, "an equivalent polypeptide" refers to a polypeptide having a certain degree of homology, or sequence identity, with the amino acid sequence of a reference polypeptide. In some aspects, the sequence identity is at least about 70%, 75%, 80%, 85%, 90%, 95%, 98%, or 99%. In some aspects, the equivalent polypeptide or polynucleotide has one, two, three, four or five addition, deletion, substitution and their combinations thereof as compared to the reference polypeptide or polynucleotide. In some aspects, the equivalent sequence retains the activity (e.g., epitope-binding) or structure (e.g., salt-bridge) of the reference sequence.

As used herein, an "antibody" or "antigen-binding polypeptide" refers to a polypeptide or a polypeptide complex that specifically recognizes and binds to an antigen. An antibody can be a whole antibody and any antigen binding fragment or a single chain thereof. Thus the term "antibody" includes any protein or peptide containing molecule that comprises at least a portion of an immunoglobulin molecule having biological activity of binding to the antigen. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The terms "antibody fragment" or "antigen-binding fragment", as used herein, is a portion of an antibody such as F(ab')2, F(ab)2, Fab', Fab, Fv, scFv and the like. Regardless of structure, an antibody fragment binds with the same antigen that is recognized by the intact antibody. The term "antibody fragment" includes aptamers, spiegelmers, and diabodies. The term "antibody fragment" also includes any synthetic or genetically engineered protein that acts like an antibody by binding to a specific antigen to form a complex.

A "single-chain variable fragment" or "scFv" refers to a fusion protein of the variable regions of the heavy (VH) and light chains (VL) of immunoglobulins. In some aspects, the regions are connected with a short linker peptide of ten to about 25 amino acids. The linker can be rich in glycine for flexibility, as well as serine or threonine for solubility, and can either connect the N-terminus of the VH with the C-terminus of the VL, or vice versa. This protein retains the specificity of the original immunoglobulin, despite removal of the constant regions and the introduction of the linker. ScFv molecules are known in the art and are described, e.g., in U.S. Pat. No. 5,892,019.

The term antibody encompasses various broad classes of polypeptides that can be distinguished biochemically. Those skilled in the art will appreciate that heavy chains are classified as gamma, mu, alpha, delta, or epsilon (, , , , ) with some subclasses among them (e.g., 1-4). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgG5, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,

8

000. The four chains are typically joined by disulfide bonds in a "Y" configuration wherein the light chains bracket the heavy chains starting at the mouth of the "Y" and continuing through the variable region.

Antibodies, antigen-binding polypeptides, variants, or derivatives thereof of the disclosure include, but are not limited to, polyclonal, monoclonal, multispecific, human, humanized, primatized, or chimeric antibodies, single chain antibodies, epitope-binding fragments, e.g., Fab, Fab' and F(ab')2, Fd, Fvs, single-chain Fvs (scFv), single-chain antibodies, disulfide-linked Fvs (sdFv), fragments comprising either a VK or VH domain, fragments produced by a Fab expression library, and anti-idiotypic (anti-Id) antibodies (including, e.g., anti-Id antibodies to LIGHT antibodies disclosed herein). Immunoglobulin or antibody molecules of the disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Light chains are classified as either kappa or lambda (, ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VK) and heavy (VH) chain portions determine antigen recognition and specificity. Conversely, the constant domains of the light chain (CK) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CK domains actually comprise the carboxy-terminus of the heavy and light chain, respectively.

As indicated above, the variable region allows the antibody to selectively recognize and specifically bind epitopes on antigens. That is, the VK domain and VH domain, or subset of the complementarity determining regions (CDRs), of an antibody combine to form the variable region that defines a three dimensional antigen-binding site. This quaternary antibody structure forms the antigen-binding site present at the end of each arm of the Y More specifically, the antigen-binding site is defined by three CDRs on each of the VH and VK chains (i.e. CDR-H1, CDR-H2, CDR-H3, CDR-L1, CDR-L2 and CDR-L3). In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., Nature 363:446-448 (1993).

In naturally occurring antibodies, the six "complementarity determining regions" or "CDRs" present in each antigen-binding domain are short, non-contiguous sequences of amino acids that are specifically positioned to form the antigen-binding domain as the antibody assumes its three dimensional configuration in an aqueous environment. The remainder of the amino acids in the antigen-binding domains, referred to as "framework" regions, show less inter-molecular variability. The framework regions largely adopt a —sheet conformation and the CDRs form loops which connect, and in some cases form part of, the —sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see "Sequences of Proteins of Immunological Interest," Kabat, E., et al., U.S. Department of Health and Human Services, (1983); and Chothia and Lesk, J. Mol. Biol., 196:901-917 (1987)).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., J. Mol. Biol. 196:901-917 (1987), which are incorporated herein by reference in their entireties. The CDR definitions according to Kabat and Chothia include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth in the table below as a comparison. The exact residue numbers which encompass a particular CDR will vary depending on the sequence and size of the CDR. Those skilled in the art can routinely determine which residues comprise a particular CDR given the variable region amino acid sequence of the antibody.

| | Kabat | Chothia |
|---|---|---|
| CDR-H1 | 31-35 | 26-32 |
| CDR-H2 | 50-65 | 52-58 |
| CDR-H3 | 95-102 | 95-102 |
| CDR-L1 | 24-34 | 26-32 |
| CDR-L2 | 50-56 | 50-52 |
| CDR-L3 | 89-97 | 91-96 |

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983).

In addition to table above, the Kabat number system describes the CDR regions as follows: CDR-H1 begins at approximately amino acid 31 (i.e., approximately 9 residues after the first cysteine residue), includes approximately 5-7 amino acids, and ends at the next tryptophan residue. CDR-H2 begins at the fifteenth residue after the end of CDR-H1, includes approximately 16-19 amino acids, and ends at the next arginine or lysine residue. CDR-H3 begins at approximately the thirty third amino acid residue after the end of CDR-H2; includes 3-25 amino acids; and ends at the sequence W-G-X-G, where X is any amino acid. CDR-L1 begins at approximately residue 24 (i.e., following a cysteine residue); includes approximately 10-17 residues; and ends at the next tryptophan residue. CDR-L2 begins at approximately the sixteenth residue after the end of CDR-L1 and includes approximately 7 residues. CDR-L3 begins at approximately the thirty third residue after the end of CDR-L2 (i.e., following a cysteine residue); includes approximately 7-11 residues and ends at the sequence F or W-G-X-G, where X is any amino acid.

Antibodies disclosed herein may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks).

As used herein, the term "heavy chain constant region" includes amino acid sequences derived from an immunoglobulin heavy chain. A polypeptide comprising a heavy chain constant region comprises at least one of. a CH1 domain, a hinge (e.g., upper, middle, and/or lower hinge region) domain, a CH2 domain, a CH3 domain, or a variant or fragment thereof. For example, an antigen-binding polypeptide for use in the disclosure may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the disclosure comprises a polypeptide chain comprising a CH3 domain. Further, an antibody for use in the disclosure may lack at least a portion of a CH2 domain (e.g., all or part of a CH2 domain). As set forth above, it will be understood by one of ordinary skill in the art that the heavy chain constant region may be modified such that they vary in amino acid sequence from the naturally occurring immunoglobulin molecule.

The heavy chain constant region of an antibody disclosed herein may be derived from different immunoglobulin molecules. For example, a heavy chain constant region of a polypeptide may comprise a CH1 domain derived from an IgG1 molecule and a hinge region derived from an IgG3 molecule. In another example, a heavy chain constant region can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain constant region" includes amino acid sequences derived from antibody light chain. Preferably, the light chain constant region comprises at least one of a constant kappa domain or constant lambda domain.

A "light chain-heavy chain pair" refers to the collection of a light chain and heavy chain that can form a dimer through a disulfide bond between the CL domain of the light chain and the CH1 domain of the heavy chain.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain"includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain"includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat et al., U.S. Dept. of Health and Human Services, "Sequences of Proteins of Immunological Interest" (1983). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains (Roux et al., J. Immunol 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CK regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant disclosure) is obtained from a second species. In certain embodiments the target binding region or site will be from a non-human source (e.g. mouse or primate) and the constant region is human.

As used herein, "percent humanization" is calculated by determining the number of framework amino acid differences (i.e., non-CDR difference) between the humanized domain and the germline domain, subtracting that number from the total number of amino acids, and then dividing that by the total number of amino acids and multiplying by 100.

By "specifically binds" or "has specificity to," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope.

For example, antibody "A" may be deemed to have a higher specificity for a given epitope than antibody "B," or antibody "A" may be said to bind to epitope "C" with a higher specificity than it has for related epitope "D."

As used herein, the terms "treat" or "treatment" refer to both therapeutic treatment and prophylactic or preventative measures, wherein the object is to prevent or slow down (lessen) an undesired physiological change or disorder, such as the progression of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on.

As used herein, phrases such as "to a patient in need of treatment" or "a subject in need of treatment" includes subjects, such as mammalian subjects, that would benefit from administration of an antibody or composition of the present disclosure used, e.g., for detection, for a diagnostic procedure and/or for treatment.

Anti-CXCR2 Antibodies and Fragments Thereof

The human CXCR2 protein is a transmembrane protein with four extracellular fragments. Each of the N-terminus and the three extra-cellular loops has been implicated in the binding of IL8. See, for example, Ahuja, S. K. et al., (1996) The Journal of biological chemistry 271, 225-232; Katancik, J. A., et al., (1997) Biochemical and Biophysical Research Communications 232, 663-668; Luo, Z. W., et al., (1997) Protein Engineering 10, 1039-1045; Berkamp, S., et al., (2017) Journal of Biomolecular Nmr 69, 111-121; Park, S. H. et al., (2017) Biophysical Journal 113, 2695-2705; Park, S. H. et al., (2011) J Mol Biol 414, 194-203; and Park, S. H. et al., (2012) Nature 491, 779-783.

Through sequence analysis and testing, the instant inventors identified the N-terminal extracellular fragment as an epitope for antibody screening. Surprisingly, a group of antibodies that were obtained from a large scale screening (from a library of $10^{11}$ candidates) and exhibited selective binding to the N-terminus (with pico-molar potency) were able to effectively block IL8 binding and potently inhibited IL8-induced neutrophil chemotaxis. The superior affinity overcame the problem that IL8 itself binds with high affinity (nano-molar), leading to a total inhibition of IL8 induced cellular functions. Further, these antibodies even showed inverse agonistic effect and markedly suppressed the intrinsic β-arrestin recruitment by CXCR2 expression. Moreover, these antibodies displayed a biased agonism effect and activated endocytosis of CXCR2, which could lead to more efficient inhibition of CXCR2-mediated pathological events.

Experimental data show that these antibodies and their antigen-binding fragments, along with those that can be obtained by additional screening, can be useful for treating diseases and conditions associated with CXCR2 signaling, such as cancer, infections, inflammatory and autoimmune diseases.

In accordance with one embodiment of the present disclosure, provided is an antibody or fragment thereof having binding specificity to a human C—X—C Motif Chemokine Receptor 2 (CXCR2) protein. In some embodiments, the binding involves one or more amino acid residues within the extracellular N-terminus (i.e., MEDFNMESDS FEDFWKGEDL SNYSYSSTLP PFLLDAAPCE PESLEINK; SEQ ID NO:15). In some embodiments, the binding at least involves one or more amino acid residues within residues 9-19 of SEQ ID NO:15 (i.e., DSFEDFWKGED, SEQ ID NO:16). In some embodiments, the binding does not involve, or at least does not require any amino acid residue outside the 48 N-terminal residues, such as those in the three extracellular loops.

In some embodiments, the binding involves (or in other words, the antibody or fragment binds to) at least one of D13, F14 and W15 of SEQ ID NO:15. In some embodiments, the binding involves at least D13. In some embodiments, the binding involves at least F14. In some embodiments, the binding involves at least W15. In some embodiments, the binding involves at least D13 and F14. In some embodiments, the binding involves at least D13 and W15. In some embodiments, the binding involves at least F14 and W15. In some embodiments, the binding involves at least another residue within SEQ ID NO:15 in addition to D13, F14 and/or W15.

In some embodiments, the binding is effective in inhibiting, competing with, or even entirely eliminating IL8 binding. In some embodiments, the antibody or fragment thereof of the present disclosure can inhibit IL8 mediated CXCR2 signaling, or even intrinsic CXCR2 signaling.

Some embodiments of the present disclosure provide an antibody or fragment thereof having binding specificity to a human C—X—C Motif Chemokine Receptor 2 (CXCR2) protein.

The antibody or fragment includes a heavy chain variable region (VH) comprising a CDR1, a CDR2 and a CDR3, and a light chain variable region (VL) comprising a CDR1, a CDR2 and a CDR3. In some embodiments, the CDRs includes sequences as shown in Table A, as well as their variants. Table B lists some variants of the VH CDR3 which have been tested in the experimental examples too.

TABLE A

| Example CDR Sequences | | |
|---|---|---|
| Name | Sequence | SEQ ID NO: |
| VH CDR1 | SYAIS | 1 |
| VH CDR2 | WINPNSGGTNYAQKFQG | 2 |
| VH CDR3 | GYCSRTRCYDY | 3 |
| VL CDR1 | TLRSGINVGAYRIY | 4 |
| VL CDR2 | YKSDSDKQQGS | 5 |
| VL CDR3 | AIWHSSAWV | 6 |

TABLE B

| Example Variants of VH CDR3 | | |
|---|---|---|
| Name | Sequence | SEQ ID NO: |
| abN48-2 | GYCSRTRCYDY | 3 |
| abN48 | GYCSSTSCYDY | 7 |

TABLE B-continued

| Example Variants of VH CDR3 | | |
|---|---|---|
| Name | Sequence | SEQ ID NO: |
| abN48-1 | GFCTRTICFVY | 8 |
| abN48-3 | GYCSFAICFDS | 9 |
| abN48-4 | GYCNRTRCYDH | 10 |
| abN48-5 | GYCSRFNCKDY | 11 |
| abN48-6 | GYCSPSGCYVY | 12 |
| abN48-7 | GYCGRARCTSF | 13 |
| abN48-8 | GYCSRSRCYDY | 14 |

In some embodiments, as shown in Table A, the VH CDR1 comprises the amino acid sequence of SEQ ID NO: 1; the VH CDR2 comprises the amino acid sequence of SEQ ID NO:2, or a variant having an amino acid substitution from SEQ ID NO:2; the VH CDR3 comprises the amino acid sequence of SEQ ID NO:3, or a variant selected from the group consisting of SEQ ID NO:7-14; the VL CDR1 comprises the amino acid sequence of SEQ ID NO:4; the VL CDR2 comprises the amino acid sequence of SEQ ID NO:5; and the VL CDR3 comprises the amino acid sequence of SEQ ID NO:6.

In some embodiments, an anti-CXCR2 antibody of the present disclosure includes the VH and VL CDR as listed in Table A, with one, two or three further modifications. Such modifications can be addition, deletion or substation of amino acids. A substitution, in some embodiments is a conservative amino acid substitution.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Non-limiting examples of conservative amino acid substitutions are provided in the table below, where a similarity score of 0 or higher indicates conservative substitution between the two amino acids.

TABLE C

Amino Acid Similarity Matrix

| | C | G | P | S | A | T | D | E | N | Q | H | K | R | V | M | I | L | F | Y | W |
|---|---|---|---|---|---|---|---|---|---|---|---|---|---|---|---|---|---|---|---|---|
| W | -8 | -7 | -6 | -2 | -6 | -5 | -7 | -7 | -4 | -5 | -3 | -3 | 2 | -6 | -4 | -5 | -2 | 0 | 0 | 17 |
| Y | 0 | -5 | -5 | -3 | -3 | -3 | -4 | -4 | -2 | -4 | 0 | -4 | -5 | -2 | -2 | -1 | -1 | 7 | 10 | |
| F | -4 | -5 | -5 | -3 | -4 | -3 | -6 | -5 | -4 | -5 | -2 | -5 | -4 | -1 | 0 | 1 | 2 | 9 | | |
| L | -6 | -4 | -3 | -3 | -2 | -2 | -4 | -3 | -3 | -2 | -2 | -3 | -3 | 2 | 4 | 2 | 6 | | | |
| I | -2 | -3 | -2 | -1 | -1 | 0 | -2 | -2 | -2 | -2 | -2 | -2 | -2 | 4 | 2 | 5 | | | | |
| M | -5 | -3 | -2 | -2 | -1 | -1 | -3 | -2 | 0 | -1 | -2 | 0 | 0 | 2 | 6 | | | | | |
| V | -2 | -1 | -1 | -1 | 0 | 0 | -2 | -2 | -2 | -2 | -2 | -2 | -2 | 4 | | | | | | |
| R | -4 | -3 | 0 | 0 | -2 | -1 | -1 | -1 | 0 | 1 | 2 | 3 | 6 | | | | | | | |
| K | -5 | -2 | -1 | 0 | -1 | 0 | 0 | 0 | 1 | 1 | 0 | 5 | | | | | | | | |
| H | -3 | -2 | 0 | -1 | -1 | -1 | 1 | 1 | 2 | 3 | 6 | | | | | | | | | |
| Q | -5 | -1 | 0 | -1 | 0 | -1 | 2 | 2 | 1 | 4 | | | | | | | | | | |
| N | -4 | 0 | -1 | 1 | 0 | 0 | 2 | 1 | 2 | | | | | | | | | | | |
| E | -5 | 0 | -1 | 0 | 0 | 0 | 3 | 4 | | | | | | | | | | | | |
| D | -5 | 1 | -1 | 0 | 0 | 0 | 4 | | | | | | | | | | | | | |
| T | -2 | 0 | 0 | 1 | 1 | 3 | | | | | | | | | | | | | | |
| A | -2 | 1 | 1 | 1 | 2 | | | | | | | | | | | | | | | |
| S | 0 | 1 | 1 | 1 | | | | | | | | | | | | | | | | |
| P | -3 | -1 | 6 | | | | | | | | | | | | | | | | | |
| G | -3 | 5 | | | | | | | | | | | | | | | | | | |
| C | 12 | | | | | | | | | | | | | | | | | | | |

TABLE D

Conservative Amino Acid Substitutions

| For Amino Acid | Substitution With |
|---|---|
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr, L-Ser, D-Ser |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

In some embodiments, the anti-CXCR2 antibody of the present disclosure includes a VH of SEQ ID NO:17 or 18, a VL of SEQ ID NO: 19, or their respective biological equivalents. A biological equivalent of a VH or VL is a sequence that includes the designated amino acids while having an overall 80%, 85%, 90%, 95%, 98% or 99% sequence identity. A biological equivalent of SEQ ID NO: 18, for instance, can be a VH that has an overall 80%, 85%, 90%, 95%, 98% or 99% sequence identity to SEQ ID NO: 18 but retains the CDRs (SEQ ID NO: 1-6 or their variants). In one embodiment, the VH has the amino acid sequence of SEQ ID NO: 18 and the VL has the amino acid sequence of SEQ ID NO: 19. In one embodiment, the VH has the amino acid sequence of SEQ ID NO: 17 and the VL has the amino acid sequence of SEQ ID NO: 19.

It will also be understood by one of ordinary skill in the art that antibodies as disclosed herein may be modified such that they vary in amino acid sequence from the naturally occurring binding polypeptide from which they were derived. For example, a polypeptide or amino acid sequence derived from a designated protein may be similar, e.g., have a certain percent identity to the starting sequence, e.g., it may be 60%, 70%, 75%, 80%, 85%, 90%, 95%, 98%, or 99% identical to the starting sequence.

In certain embodiments, the antibody comprises an amino acid sequence or one or more moieties not normally associated with an antibody. Exemplary modifications are described in more detail below. For example, an antibody of the disclosure may comprise a flexible linker sequence, or may be modified to add a functional moiety (e.g., PEG, a drug, a toxin, or a label).

Antibodies, variants, or derivatives thereof of the disclosure include derivatives that are modified, i.e., by the covalent attachment of any type of molecule to the antibody such that covalent attachment does not prevent the antibody from binding to the epitope. For example, but not by way of limitation, the antibodies can be modified, e.g., by glycosylation, acetylation, pegylation, phosphorylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the antibodies may contain one or more non-classical amino acids.

In some embodiments, the antibodies may be conjugated to therapeutic agents, prodrugs, peptides, proteins, enzymes, viruses, lipids, biological response modifiers, pharmaceutical agents, or PEG.

The antibodies may be conjugated or fused to a therapeutic agent, which may include detectable labels such as radioactive labels, an immunomodulator, a hormone, an enzyme, an oligonucleotide, a photoactive therapeutic or diagnostic agent, a cytotoxic agent, which may be a drug or a toxin, an ultrasound enhancing agent, a non-radioactive label, a combination thereof and other such agents known in the art.

Polynucleotides Encoding the Antibodies and Methods of Preparing the Antibodies

The present disclosure also provides isolated polynucleotides or nucleic acid molecules encoding the antibodies, variants or derivatives thereof of the disclosure. The polynucleotides of the present disclosure may encode the entire heavy and light chain variable regions of the antigen-binding polypeptides, variants or derivatives thereof on the same polynucleotide molecule or on separate polynucleotide molecules. Additionally, the polynucleotides of the present disclosure may encode portions of the heavy and light chain variable regions of the antigen-binding polypeptides, variants or derivatives thereof on the same polynucleotide molecule or on separate polynucleotide molecules.

Methods of making antibodies are well known in the art and described herein. In certain embodiments, both the variable and constant regions of the antigen-binding polypeptides of the present disclosure are fully human. Fully human antibodies can be made using techniques described in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140 which are incorporated by reference in their entireties.

In certain embodiments, the prepared antibodies will not elicit a deleterious immune response in the animal to be treated, e.g., in a human. In one embodiment, antigen-binding polypeptides, variants, or derivatives thereof of the disclosure are modified to reduce their immunogenicity using art-recognized techniques. For example, antibodies can be humanized, primatized, deimmunized, or chimeric antibodies can be made. These types of antibodies are derived from a non-human antibody, typically a murine or primate antibody, that retains or substantially retains the antigen-binding properties of the parent antibody, but which is less immunogenic in humans. This may be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues. Such methods are disclosed in Morrison et al., *Proc. Natl. Acad. Sci. USA* 57:6851-6855 (1984); Morrison et al., *Adv. Immunol.* 44:65-92 (1988); Verhoeyen etal., *Science* 239:1534-1536 (1988); *Padlan, Molec. Immun.* 25:489-498 (1991); *Padlan, Molec. Immun.* 31:169-217 (1994), and U.S. Pat. Nos. 5,585,089, 5,693, 761, 5,693,762, and 6,190,370, all of which are hereby incorporated by reference in their entirety.

De-immunization can also be used to decrease the immunogenicity of an antibody. As used herein, the term "de-immunization"includes alteration of an antibody to modify T-cell epitopes (see, e.g., International Application Publication Nos.: WO/9852976 A1 and WO/0034317 A2). For example, variable heavy chain and variable light chain sequences from the starting antibody are analyzed and a human T-cell epitope "map" from each V region showing the location of epitopes in relation to complementarity-determining regions (CDRs) and other key residues within the sequence is created. Individual T-cell epitopes from the T-cell epitope map are analyzed in order to identify alternative amino acid substitutions with a low risk of altering activity of the final antibody. A range of alternative variable heavy and variable light sequences are designed comprising combinations of amino acid substitutions and these sequences are subsequently incorporated into a range of binding polypeptides. Typically, between 12 and 24 variant antibodies are generated and tested for binding and/or function. Complete heavy and light chain genes comprising modified variable and human constant regions are then cloned into expression vectors and the subsequent plasmids introduced into cell lines for the production of whole antibody. The antibodies are then compared in appropriate biochemical and biological assays, and the optimal variant is identified.

The binding specificity of antigen-binding polypeptides of the present disclosure can be determined by in vitro assays such as immunoprecipitation, radioimmunoassay (RIA) or enzyme-linked immunoabsorbent assay (ELISA).

Alternatively, techniques described for the production of single-chain units (U.S. Pat. No. 4,694,778; Bird, *Science* 242:423-442 (1988); Huston et al., *Proc. Natl. Acad. Sci. USA* 55:5879-5883 (1988); and Ward et al., *Nature* 334:544-554 (1989)) can be adapted to produce single-chain units of the present disclosure. Single-chain units are formed by linking the heavy and light chain fragments of the Fv region via an amino acid bridge, resulting in a single-chain fusion peptide. Techniques for the assembly of functional Fv fragments in *E. coli* may also be used (Skerra et al., *Science* 242: 1038-1041 (1988)).

Examples of techniques which can be used to produce single-chain Fvs (scFvs) and antibodies include those described in U.S. Pat. Nos. 4,946,778 and 5,258,498; Huston et al., *Methods in Enzymology* 203:46-88 (1991); Shu et al., *Proc. Natl. Sci. USA* 90:1995-1999 (1993); and Skerra et al., *Science* 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., Morrison, *Science* 229:1202 (1985); Oi et al., *BioTechniques* 4:214 (1986); Gillies et al., *J. Immunol. Methods* 125:191-202 (1989); U.S. Pat. Nos. 5,807,715; 4,816,567; and 4,816397, which are incorporated herein by reference in their entireties.

Humanized antibodies are antibody molecules derived from a non-human species antibody that bind the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen-binding. These framework substitutions are identified by methods well known in the art, e.g., by modeling of the interactions of the CDR and framework residues to identify framework residues important for antigen-binding and sequence comparison to identify unusual framework residues at particular positions. (See, e.g., Queen et al., U.S. Pat. No. 5,585,089; Riechmann et al., *Nature* 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, *Molecular Immunology* 28(4/5):489-498 (1991); Studnicka et al., *Protein Engineering* 7(6):805-814 (1994); Roguska. et al., *Proc.*

*Natl. Sci. USA* 91:969-973 (1994)), and chain shuffling (U.S. Pat. No. 5,565,332, which is incorporated by reference in its entirety).

Completely human antibodies are particularly desirable for therapeutic treatment of human patients. Human antibodies can be made by a variety of methods known in the art including phage display methods using antibody libraries derived from human immunoglobulin sequences.

See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a desired target polypeptide. Monoclonal antibodies directed against the antigen can be obtained from the immunized, transgenic mice using conventional hybridoma technology. The human immunoglobulin transgenes harbored by the transgenic mice rearrange during B-cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar *Int. Rev. Immunol.* 73:65-93 (1995). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety. In addition, companies such as Abgenix, Inc. (Freemont, Calif.) and GenPharm (San Jose, Calif.) can be engaged to provide human antibodies directed against a selected antigen using technology similar to that described above.

Completely human antibodies which recognize a selected epitope can also be generated using a technique referred to as "guided selection." In this approach a selected non-human monoclonal antibody, e.g., a mouse antibody, is used to guide the selection of a completely human antibody recognizing the same epitope. (Jespers et al., *Bio Technology* 72:899-903 (1988). See also, U.S. Pat. No. 5,565,332, which is incorporated by reference in its entirety.)

In another embodiment, DNA encoding desired monoclonal antibodies may be readily isolated and sequenced using conventional procedures (e.g., by using oligonucleotide probes that are capable of binding specifically to genes encoding the heavy and light chains of murine antibodies). The isolated and subcloned hybridoma cells serve as a preferred source of such DNA. Once isolated, the DNA may be placed into expression vectors, which are then transfected into prokaryotic or eukaryotic host cells such as *E. coli* cells, simian COS cells, Chinese Hamster Ovary (CHO) cells or myeloma cells that do not otherwise produce immunoglobulins. More particularly, the isolated DNA (which may be synthetic as described herein) may be used to clone constant and variable region sequences for the manufacture antibodies as described in Newman et al., U.S. Pat. No. 5,658,570, filed Jan. 25, 1995, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As will be discussed in more detail below, transformed cells expressing the desired antibody may be grown up in relatively large quantities to provide clinical and commercial supplies of the immunoglobulin.

Additionally, using routine recombinant DNA techniques, one or more of the CDRs of the antigen-binding polypeptides of the present disclosure, may be inserted within framework regions, e.g., into human framework regions to humanize a non-human antibody. The framework regions may be naturally occurring or consensus framework regions, and preferably human framework regions (see, e.g., Chothia et al., *J. Mol. Biol.* 278:457-479 (1998) for a listing of human framework regions). Preferably, the polynucleotide generated by the combination of the framework regions and CDRs encodes an antibody that specifically binds to at least one epitope of a desired polypeptide, e.g., LIGHT. Preferably, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present disclosure and within the skill of the art.

In addition, techniques developed for the production of "chimeric antibodies" (Morrison et al., *Proc. Natl. Acad. Sci. USA*:851-855 (1984); Neuberger et al., *Nature* 372:604-608 (1984); Takeda et al., *Nature* 314:452-454 (1985)) by splicing genes from a mouse antibody molecule, of appropriate antigen specificity, together with genes from a human antibody molecule of appropriate biological activity can be used. As used herein, a chimeric antibody is a molecule in which different portions are derived from different animal species, such as those having a variable region derived from a murine monoclonal antibody and a human immunoglobulin constant region.

Yet another highly efficient means for generating recombinant antibodies is disclosed by Newman, *Biotechnology* 10: 1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

Alternatively, antibody-producing cell lines may be selected and cultured using techniques well known to the skilled artisan. Such techniques are described in a variety of laboratory manuals and primary publications. In this respect, techniques suitable for use in the disclosure as described below are described in *Current Protocols in Immunology*, Coligan et al., Eds., Green Publishing Associates and Wiley-Interscience, John Wiley and Sons, New York (1991) which is herein incorporated by reference in its entirety, including supplements.

Additionally, standard techniques known to those of skill in the art can be used to introduce mutations in the nucleotide sequence encoding an antibody of the present disclosure, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference variable heavy chain region, CDR-H1, CDR-H2, CDR-H3, variable light chain region, CDR-L1, CDR-L2, or CDR-L3. Alternatively, mutations can be introduced randomly along all or part of the coding sequence, such as by saturation mutagenesis, and the resultant mutants can be screened for biological activity to identify mutants that retain activity.

Cancer Treatment

As described herein, the antibodies, variants or derivatives of the present disclosure may be used in certain treatment and diagnostic methods.

The present disclosure is further directed to antibody-based therapies which involve administering the antibodies or fragments of the disclosure to a patient, such as a human patient, for treating one or more of the disorders or conditions described herein. Therapeutic products of the disclosure include, but are not limited to, antibodies of the disclosure (including variants and derivatives thereof as described herein) and nucleic acids or polynucleotides encoding antibodies of the disclosure (including variants and derivatives thereof as described herein).

The antibodies and fragments of the disclosure can be used to treat or inhibit cancer. The chemokine receptor CXCR2 and its ligands are implicated in the progression of tumors and various inflammatory diseases. Activation of the CXCLs/CXCR2 axis activates multiple signaling pathways, including the PI3K, p38/ERK, and JAK pathways, and regulates cell survival and migration. The CXCLs/CXCR2 axis plays a vital role in the tumor microenvironment and in recruiting neutrophils to inflammatory sites. Extensive infiltration of neutrophils during chronic inflammation is one of the most important pathogenic factors in various inflammatory diseases.

Tumors that can be suitably treated with the antibodies or fragments of the present disclosure include bladder cancer, non-small cell lung cancer, renal cancer, breast cancer, urethral cancer, colorectal cancer, head and neck cancer, squamous cell cancer, Merkel cell carcinoma, gastrointestinal cancer, stomach cancer, esophageal cancer, ovarian cancer, renal cancer, and small cell lung cancer. Accordingly, the presently disclosed antibodies can be used for treating any one or more such cancers.

Cellular therapies, such as chimeric antigen receptor (CAR) T-cell therapies, are also provided in the present disclosure. A suitable cell can be used, that is put in contact with an anti-CXCR2 antibody of the present disclosure (or alternatively engineered to express an anti-CXCR2 antibody of the present disclosure). Upon such contact or engineering, the cell can then be introduced to a cancer patient in need of a treatment. The cancer patient may have a cancer of any of the types as disclosed herein. The cell (e.g., T cell) can be, for instance, a tumor-infiltrating T lymphocyte, a CD4+ T cell, a CD8+ T cell, or the combination thereof, without limitation.

In some embodiments, the cell was isolated from the cancer patient him- or her-self. In some embodiments, the cell was provided by a donor or from a cell bank. When the cell is isolated from the cancer patient, undesired immune reactions can be minimized.

Additional diseases or conditions associated with increased cell survival, that may be treated, prevented, diagnosed and/or prognosed with the antibodies or variants, or derivatives thereof of the disclosure include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, thyroid cancer, endometrial cancer, melanoma, prostate cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

Treatment of Inflammatory Diseases

As demonstrated in the experimental examples, the antibodies of the present disclosure can change immune response which can then be useful for treating inflammatory diseases and conditions, autoimmune diseases, and infections.

In some embodiments, the inflammatory disease or condition to be treated by the disclosed antibodies, fragments and compositions includes one or more of Alzheimer's disease, Addison's disease, atherosclerosis, ankylosing spondylitis, arthritis, osteoarthritis (OA), rheumatoid arthritis (RA), psoriatic arthritis (PA), ankylosing spondylitis, asthma, atherosclerosis, chronic obstructive pulmonary disease(COPD), Crohn's disease, colitis, dermatitis, diverticulitis, fibromyalgia, hepatitis, irritable bowel syndrome (IBS), systemic lupus erythematous (SLE), nephritis, Parkinson's disease (PD), vasculitis, and ulcerative colitis.

In some embodiments, the autoimmune disease or condition to be treated by the disclosed antibodies, fragments and compositions includes one or more of alopecia areata, autoimmune hemolytic anemia, autoimmune hepatitis, dermatomyositis, diabetes (type 1), celiac disease, autoimmune juvenile idiopathic arthritis, glomerulonephritis, Graves' disease, Guillain-Barre syndrome, idiopathic thrombocytopenic purpura, myasthenia gravis, autoimmune myocarditis, multiple sclerosis, pemphigus/pemphigoid, pernicious anemia, polyarteritis nodosa, polymyositis, primary biliary cirrhosis, psoriasis, rheumatoid arthritis, scleroderma/systemic sclerosis, Sjögren's syndrome, systemic lupus erythematosus, autoimmune thyroiditis, Hashimoto's thyroiditis, autoimmune uveitis, vitiligo, and granulomatosis with polyangiitis (Wegener's).

Rheumatoid arthritis (RA) is a long-term autoimmune disorder that primarily affects joints. It typically results in warm, swollen, and painful joints. Pain and stiffness often worsen following rest. Most commonly, the wrist and hands are involved, with the same joints typically involved on both sides of the body. The disease may also affect other parts of the body. While the cause of rheumatoid arthritis is not clear, it is believed to involve a combination of genetic and environmental factors. The underlying mechanism involves the body's immune system attacking the joints. This results in inflammation and thickening of the joint capsule. The goals of treatment are to reduce pain, decrease inflammation, and improve a person's overall functioning. Pain medications, steroids, and NSAIDs are frequently used to help with symptoms. A group of medications called disease-modifying antirheumatic drugs (DMARDs), such as hydroxychloroquine and methotrexate, may be used to try to slow the progression of disease.

Osteoarthritis (OA) is a type of joint disease that results from breakdown of joint cartilage and underlying bone. The most common symptoms are joint pain and stiffness. Initially, symptoms may occur only following exercise, but over time may become constant. Other symptoms may include joint swelling, decreased range of motion, and when the back is affected weakness or numbness of the arms and legs. Causes include previous joint injury, abnormal joint or limb development, and inherited factors. Risk is greater in those who are overweight, have one leg of a different length, and have jobs that result in high levels of joint stress. Osteoarthritis is believed to be caused by mechanical stress on the joint and low grade inflammatory processes. Treatment includes exercise, efforts to decrease joint stress, support groups, and pain medications.

Multiple sclerosis (MS) is a demyelinating disease in which the insulating covers of nerve cells in the brain and spinal cord are damaged. This damage disrupts the ability of parts of the nervous system to communicate, resulting in a range of signs and symptoms, including physical, mental, and sometimes psychiatric problems. Specific symptoms can include double vision, blindness in one eye, muscle weakness, trouble with sensation, or trouble with coordination. While the cause is not clear, the underlying mechanism is thought to be either destruction by the immune system or failure of the myelin-producing cells. There is no known cure for multiple sclerosis. Treatments attempt to improve function after an attack and prevent new attacks.

Asthma is a common long-term inflammatory disease of the airways of the lungs. It is characterized by variable and recurring symptoms, reversible airflow obstruction, and bronchospasm. Symptoms include episodes of wheezing, coughing, chest tightness, and shortness of breath. Asthma is thought to be caused by a combination of genetic and environmental factors. Environmental factors include exposure to air pollution and allergens. Asthma is classified according to the frequency of symptoms, forced expiratory volume in one second (FEV1), and peak expiratory flow rate. It may also be classified as atopic or non-atopic, where atopy refers to a predisposition toward developing a type 1 hypersensitivity reaction. There is no cure for asthma. Symptoms can be prevented by avoiding triggers, such as allergens and irritants, and by the use of inhaled corticosteroids. Long-acting beta agonists (LABA) or antileukotriene agents may be used in addition to inhaled corticosteroids if asthma symptoms remain uncontrolled. Treatment of rapidly worsening symptoms is usually with an inhaled short-acting beta-2 agonist such as salbutamol and corticosteroids taken by mouth. In very severe cases, intravenous corticosteroids, magnesium sulfate, and hospitalization may be required.

Chronic obstructive pulmonary disease(COPD) is a type of obstructive lung disease characterized by long-term poor airflow. COPD can include two main conditions, emphysema and chronic bronchitis. In emphysema, the walls between many of the air sacs are damaged. As a result, the air sacs lose their shape and become floppy. This damage also can destroy the walls of the air sacs, leading to fewer and larger air sacs instead of many tiny ones. If this happens, the amount of gas exchange in the lungs is reduced. In chronic bronchitis, the lining of the airways stays constantly irritated and inflamed, and this causes the lining to swell. Lots of thick mucus forms in the airways, making it hard to breathe. There is no known cure for COPD, but the symptoms are treatable and its progression can be delayed.
Administration Methods of administration of the antibodies, variants or include but are not limited to intradermal, intramuscular, intraperitoneal, intravenous, subcutaneous, intranasal, epidural, and oral routes. The antigen-binding polypeptides or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Thus, pharmaceutical compositions containing the antigen-binding polypeptides of the disclosure may be administered orally, rectally, parenterally, intracistemally, intravaginally, intraperitoneally, topically (as by powders, ointments, drops or transdermal patch), bucally, or as an oral or nasal spray.

The term "parenteral" as used herein refers to modes of administration which include intravenous, intramuscular, intraperitoneal, intrasternal, subcutaneous and intra-articular injection and infusion.

Administration can be systemic or local. In addition, it may be desirable to introduce the antibodies of the disclosure into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

It may be desirable to administer the antibodies polypeptides or compositions of the disclosure locally to the area in need of treatment; this may be achieved by, for example, and not by way of limitation, local infusion during surgery, topical application, e.g., in conjunction, with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the disclosure, care must be taken to use materials to which the protein does not absorb.

In another embodiment, the antibodies or composition can be delivered in a vesicle, in particular a liposome (see Langer, 1990, *Science* 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

As a general proposition, the dosage administered to a patient of the antigen-binding polypeptides of the present disclosure is typically 0.1 mg/kg to 100 mg/kg of the patient's body weight, between 0.1 mg/kg and 20 mg/kg of the patient's body weight, or 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the disclosure may be reduced by enhancing uptake and tissue penetration (e.g., into the brain) of the antibodies by modifications such as, for example, lipidation.

The methods for treating an infectious or malignant disease, condition or disorder comprising administration of an antibody, variant, or derivative thereof of the disclosure are typically tested in vitro, and then in vivo in an acceptable animal model, for the desired therapeutic or prophylactic activity, prior to use in humans. Suitable animal models, including transgenic animals, are well known to those of ordinary skill in the art. For example, in vitro assays to demonstrate the therapeutic utility of antigen-binding polypeptide described herein include the effect of an antigen-binding polypeptide on a cell line or a patient tissue sample.

The effect of the antigen-binding polypeptide on the cell line and/or tissue sample can be determined utilizing techniques known to those of skill in the art, such as the assays disclosed elsewhere herein. In accordance with the disclosure, in vitro assays which can be used to determine whether administration of a specific antigen-binding polypeptide is indicated, include in vitro cell culture assays in which a patient tissue sample is grown in culture, and exposed to or otherwise administered a compound, and the effect of such compound upon the tissue sample is observed.

Various delivery systems are known and can be used to administer an antibody of the disclosure or a polynucleotide encoding an antibody of the disclosure, e.g., encapsulation in liposomes, microparticles, microcapsules, recombinant cells capable of expressing the compound, receptor-mediated endocytosis (see, e.g., Wu and Wu, 1987, *J. Biol. Chem.* 262:4429-4432), construction of a nucleic acid as part of a retroviral or other vector, etc.

Diagnostic Methods

In some embodiments, the antibodies of the present disclosure can be used for diagnostic and prognostic purposes. In some embodiments, a method of detecting expression of CXCR2 in a sample is provided, comprising contacting the sample with an antibody or fragment thereof of the present disclosure under conditions for the antibody or fragment thereof to bind to the CXCR2, and detecting the binding which indicates expression of CXCR2 in the sample.

A sample that preferably includes a cell can be obtained from a patient, which can be a cancer patient or a patient desiring diagnosis. The cell be a cell of a tumor tissue or a tumor block, a blood sample, a urine sample or any sample from the patient. Upon optional pre-treatment of the sample, the sample can be incubated with an antibody of the present disclosure under conditions allowing the antibody to interact with a CXCR2 protein potentially present in the sample. Methods such as ELISA can be used, taking advantage of the anti-CXCR2 antibody, to detect the presence of the CXCR2 protein in the sample.

Presence of the CXCR2 protein in the sample (optionally with the amount or concentration) can be used for diagnosis of cancer, as an indication that the patient is suitable for a treatment with the antibody, or as an indication that the patient has (or has not) responded to a cancer treatment. For a prognostic method, the detection can be done at once, twice or more, at certain stages, upon initiation of a cancer treatment to indicate the progress of the treatment.

Compositions

The present disclosure also provides pharmaceutical compositions. Such compositions comprise an effective amount of an antibody, and an acceptable carrier. In some embodiments, the composition further includes a second anticancer agent (e.g., an immune checkpoint inhibitor).

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. Further, a "pharmaceutically acceptable carrier" will generally be a non-toxic solid, semisolid or liquid filler, diluent, encapsulating material or formulation auxiliary of any type.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences by E. W. Martin, incorporated herein by reference. Such compositions will contain a therapeutically effective amount of the antigen-binding polypeptide, preferably in purified form, together with a suitable amount of carrier so as to provide the form for proper administration to the patient. The formulation should suit the mode of administration. The parental preparation can be enclosed in ampoules, disposable syringes or multiple dose vials made of glass or plastic.

In an embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

EXAMPLES

Example 1: Experimental Procedures

Cell Culture

HEK293F cells (#R79007; Thermo Fisher Scientific) were cultured in FreeStyle 293 Expression Medium (#12338-026; Thermo Fisher Scientific). U2OS cell line (ATCC-HTB96; cell bank of Chinese Academy of Science, Shanghai) was maintained in McCoy's 5A Medium (#16600-082, Gibco) containing 10% (vol/vol) FBS. Tango™ CXCR2-bla U2OS cell line (#K1807; Thermo Fisher Scientific) was maintained in growth medium based on McCoy's 5A Medium according to manufacturer's instruction. CHO-K1 cells were cultured in F12K medium (#21127022; Thermo Fisher Scientific) containing 10% (v/v) FBS.

Combinatorial Antibody Library Panning

Peptide of 48 amino acids the same to N-terminal extracellular domain of human CXCR2 (MEDFN-MESDSFEDFWKGEDLSNYSYSSTLPPFLLDAAP-CEPESLEINK; SEQ ID NO:15) with biotin labeled on its N-terminus (pepN48) was synthesized (Chinese Peptide) as antigen for phage panning. The panning procedure followed a modified protocol as described previously. Briefly, phage particles displaying a combinatorial scFv antibody library with ~10¹¹ diversity were incubated with antigen pepN48. Then streptavidin-coated magnetic beads (#21925; Pierce) were added into the solution to pull down the phage-bound biotinylated antigen. Bound phages were eluted by glycine-HCl (pH 2.0) after washing out unbound phage and used for infection of XL-1 blue cells (#200228; Agilent). The infected cells were used to generate phage particles for next round of panning with help of helper phage VCSM13 (#200251; Agilent). After 3 rounds of enrichment, colonies were picked and tested by phage ELISA, after which all positive clones were sequenced. The international ImMunoGeneTics information system (IMGT) was used for contig analysis of sequences of these colonies. Nine distinct scFv sequences were highly enriched.

ELISA

Avidin (#21121; Pierce) was diluted in Carbonate-Bicarbonate buffer (#C3041; Sigma) to final concentration of 2 ng/μl. The 96-well ELISA plates (Coming Costar) were coated by the avidin solution (25 μl/well) at 4° C. overnight. Wells were washed once with 150 μl/well PBST buffer (0.05% TWEEN20 in PBS). 50 ng of antigen dissolved in PBS (2 ng/μl) was added to each well and incubated for 30 min at room temperature. Wells were washed 3 times with PBST and blocked with M-PBST (3% milk in PBST, 150 μl/well) at 37° C. for 5 min. After removal of M-PBST buffer, 25 μl of antibody solution (diluted in M-PBST buffer in proper concentration) was added into each well and incubated for 1 h at room temperature, followed by repeated washes with PBST for 5 times. Anti-M13 HRP-conjugated secondary antibody (1:3,000 dilution; #27-9421-01, GE) or the anti-human Fc HRP-conjugated secondary antibody (1:3,000 dilution; #A0170, Sigma) was added into the wells and incubated for 1 h at room temperature. Then the wells were washed five times with PBST, followed by incubation with 50 μl/well ABTS solution (#11684302001; Roche) at room temperature for 20 min. Absorbance of each well was measured at 405 nm on a plate reader (EnSpire; PerkinElmer).

Expression and Purification of Antibodies

DNA sequences encoding the candidate scFv antibodies were cloned into a pFuse expression vector (#pfuse-hglfc2; InvivoGen) for expression of scFv-Fc protein with entire Fc domain of human IgG1. For antibodies with the full-length IgG1 form, variable regions of heavy chain and light chain ($V_H$ & $V_L$) from the scFv sequence were cloned into plasmids with entire constant domains of heavy chain and light chain ($C_H$ & $C_L$) respectively. The antibodies were expressed through transfection of the scFv-Fc expression plasmid, or co-transfection of equal molar of heavy chain and light plasmids for full length antibody, into HEK293F cells followed by cell culture for 5 days. Antibodies in the medium were purified with a HiTrap Protein A HP column (#17-0403-03; GE Healthcare) by ÄKTAxpress purifier (GE Healthcare). Purified antibodies were concentrated and stored in PBS buffer (pH7.4) at −80° C.

Size-Exclusion-Column HPLC (SEC-HPLC)

SEC-HPLC experiment was carried out to determine the thermo-stability and homogeneity of purified recombinant antibodies. Briefly, antibody solutions were first concentrated to 20 mg/mL, and incubated at 42° C. for 5 days. The resulting antibody solutions were analyzed by HPLC on a SEC column (Nanofilm SEC-250) with a running buffer of 0.05% DDM/0.01% CHS in Tris (pH 8.1). Aggregation and degradation were evaluated by the protein homogeneity results.

Flow-Cytometry

Cells were transfected with expression plasmids containing target membrane proteins. After 24 hours, cells were detached from dish and re-suspended in a FACS buffer (0.5% BSA in PBS, with 2 mM EDTA). 500,000 cells per tube were incubated with 2 μg/mL corresponding antibody in a FACS buffer at 4° C. for 15 min. The resulting cells were washed twice with a FACS buffer, and then incubated with 2 μg/mL secondary antibody, Alexa Fluor™ 488 goat anti-human IgG (H+L) (#A11013; Life Technologies), at 4° C. for 15 min. After two washes with the FACS buffer, cells were re-suspended in PBS and analyzed by CytoFLEX S (Beckman Coulter).

Immunofluorescence Assay

Cells were plated and cultured in poly-D-lysine-coated glass-bottom 96-well microtiter plates (PerkinElmer). Plasmids expressing target membrane proteins were transfected into cells using Lipofectamine 3000. 24 hours after transfection, cells were fixed by 4% paraformaldehyde for 20 min at room temperature, followed by 3 washes with PBS, 5 min each.

Cells were then blocked with 1% BSA (dissolved in PBS) for 30 min at 37° C. After blocking, cells were incubated with corresponding antibodies (diluted in 1% BSA/PBS, 2 µg/ml) at 4° C. overnight. 2 µg/mL secondary antibody, Alexa Fluor™ 488 goat anti-human IgG (H+L) (#A11013; Life Technologies), was then mixed with cells in a 1% BSA PBS buffer at room temperature for 1 hour. DAPI (#10236276001; Roche) was added for nuclei staining. After 3 times of washing with PBS, the stained cells were kept in PBS for immunofluorescence analysis on a confocal microscopy (ZEISS LSM710).

Surface-Plasmon-Resonance (SPR)

Biotinylated antigen (purified protein or peptide) was loaded on the streptavidin coated surface of a SA biosensor chip (GE healthcare) to form a single molecular layer. The interaction between antibody and antigen was carried out on a Biacore T200 system (GE Healthcare). Briefly, testing antibody were serially diluted in a running buffer, HBS-EP+ buffer (GE Healthcare), to different concentrations of 0.5, 1, 2, 5, 10 nM, and flowed through the surface of chip for the detection of molecular interaction between antigen and antibody. Kinetics of binding/dissociation were measured and fitted to an appropriate protein-protein interaction model to calculate the corresponding binding constant ($K_D$).

Affinity Maturation Using Yeast Display

DNA sequences of heavy chain and light chain of the selected antibody (abN48-IgG1) were cloned into a yeast surface display vector pYD-HA. Primers containing a randomly mutated H-CDR3 region were used to generate CDR3-diversified heavy chain with overlap PCR. The CDR3-diversified heavy chain fragments and linearized backbone plasmid were transfected into EBY100 yeast cells by electroporation to complete construction of the yeast-based Fab mutagenic library using the intrinsic homologous recombination strategy of yeast cell.

EBY100 yeast cells transformed with the mutagenic library were grown in SD/Trp-media (#630308; Clontech) to $OD_{600}=1$ and then induced in SG/R-CAA medium at 20° C. for 18-24 h with shaking. After the cells were washed by FACS buffer (0.5% B SAin PBS, with 2 mM EDTA), pepN48 and anti-c-myc chicken IgY fraction (#A21281; Life Technologies) were added into the cell suspension (1:500 dilution) and incubated for 30 min at room temperature. Cells were washed for 3 times with FACS buffer, then the R-phycoerythrin conjugated Streptavidin (#21627, Thermo Fisher Scientific) and FITC conjugated goat anti-chicken secondary antibody (#PA1-28794; Invitrogen) were added to the cell suspension (1:500 dilutions) and incubated at 4° C. for 30 min. Finally cells were analyzed by a flow cytometer (CytoFLEX S; Beckman Coulter) after being washed for 3 times with FACS buffer. For library screen, fluorescence-labeled yeast cells of each round were sorted with a BD FACSAria III flow cytometer (FACSAria III; BD). Concentration of pepN48 was decreased gradually in each round of selection from 1 nM to 0.25 nM.

Tango Assay

In a Tango assay, hCXCR2 was fused to an exogenous transcription factor, and in between, a specific cleavage sequence for a non-native protease fused with β-arrestin was linked. Once ligands bound to hCXCR2 and triggered desensitization of membrane, intracellular arrestin-protease fusion protein is recruited to the activated receptor, the fused transcription factor was cleaved by the protease, entered into nucleus, and resulted in activation of a reporter gene with fluorescence emission at 520 nm wavelength. Tango assay was performed following the manufacturer's instruction of LiveBLAzer FRET-B/G Loading Kit (#K1030; Invitrogen). Briefly, Tango CXCR2-bla U2OS cells were plated at 20,000 cells per well on a CellCarrier-96 (PerkinElmer) plate and cultured in a media at 37° C. /5% $CO_2$ overnight. The resulting cells were re-inoculated into the assay medium provided in the kit, and incubated for 48 hours at 37° C./5% $CO_2$. Different concentrations of ligands such as IL8, Groα (CXCL1) and antibody ligands were mixed with the above cells at 37° C. /5% $CO_2$ overnight to measure their agonist effects.

For inhibition studies of abN48-IgG1 and abN48-2-IgG1, cells were first treated with different concentrations of antibody for 30 min at 37° C. /5% $CO_2$, then 20 nM IL8 or Groα (CXCL1) ($EC_{80}$) was added and incubated for overnight at 37° C. /5% $CO_2$. Before lysing the cells, detection substrate mixture was added and incubated with cells for 2 hours at room temperature. The fluorescence emission at wavelength 520 nm upon excitation at wavelength 460 nm were recorded and quantitated on a fluorescence plate reader (EnVision, PerkinElmer).

Calcium Influx

Calcium ion influx assays were carried out in the in-house CHO cells stably expressed both hCXCR2 and Gα16 protein. Cells were plated at 20,000 cells per well in a 384-well plate and cultured for 4-6 hours in growth media supplemented with 1% FBS. Media was removed, and the resulting cells were washed twice with HBSS buffer. 25 µL of the loading solution containing freshly prepared calcium dye, Fluo-4 Direct™ (#F10471; Invitrogen), were added into each well and incubated for 30 min at 37° C. The assay plate was allowed to equilibrate to room temperature before subject to FLIPR detection. For the measurement of agonist effect, 5 µL ligand stocks (in HBSS buffer) of different concentrations for IL8, Groα (CXCL1), and combinatorial antibodies were mixed quickly into each well containing the dye-loaded cells, and recorded immediately on a FLIPR reader (Tetra Multi-Mode Microplate Reader, Molecular Devices) at wavelength 494 nm (excitation) and 516 nm (emission). The final assay concentrations are 100, 25, 6.2, 1.6, 0.39, 0.098, 0.024, 0.0061 nM for IL8 and Groα (CXCL1); 3600, 900, 225, 56, 14, 3.5, 0.88, 0.22 nM for abN48-IgG1and abN48-2-IgG.

For inhibition studies of abN48-IgG1 and abN48-2-IgG1, 5 µL HBSS stocks with different concentrations of abN48-IgG1 and abN48-2-IgG1 were first mixed into each corresponding well containing 25 µL dye-loaded CHO cells, followed by equilibrium at room temperature for 30 minutes. Ca2+influx signal was initiated by quick mixing of 5 µL HBSS stock of IL-8 (final concentration in the assay of 2.5 nM) or Groα (CXCL1) (final concentration in the assay of 7 nM) into each well on FLIPR. The final concentrations of abN48-IgG1 and abN48-2-IgG1 in the assay were 3600 nM, 1200, 400, 130, 44, 15, 4.9, 1.6 nM for IL8 inhibition, and 3600, 900, 225, 56, 14, 3.5, 0.88, 0.22 nM for Groα (CXCL1) inhibition, respectively. Fluorescent signals of $Ca^{2+}$ influx were recorded in real time as described above.

Internalization of hCXCR2

A modified method utilizing an adaptor-toxin fusion protein, AL2-PE38KDEL, which binds specifically to IgG and forms an immunotoxin complex, was used to measure the antibody stimulated CXCR2 endocytosis (Hou, S.-C. et al., (2016). Scientific reports 6, 31878). The resulting immunotoxin complex induces cell death when enters into the cells. Briefly, AL2-PE38KDEL was added to antibody solutions at 1:1 molar ratio, and incubated at room temperature for 1 hour to generate the immunotoxin complex. The immunotoxin was mixed with cells overexpressed with hCXCR2 at different final concentration, and incubated for 4 hours at room temperature. The resulting cells were re-inoculated into a fresh media, and cultivated for 3 days at 37° C. /5% $CO_2$. WST-1 (#W201-12; Dojindo) was used to determine the cell viability by measuring the absorbance at 450 nm according to manufacturer protocol.

Neutrophil Chemotaxis

Neutrophil migration was detected with 24-well transwell chambers with 8-μm pore size membranes (#3422, Corning Costar). Primary human neutrophils (#PBN-1F, MT-BIO) were suspended in chemotaxis medium (RPMI 1640 medium with 0.5% BSA) to $5\times10^5$ cells/ml. These neutrophil samples were incubated with abN48-IgG1, abN48-2-IgG1, isotype antibody, CXCR1/2 inhibitor Navarixin (MK7123, #HY-10198, MedChemExpress) at different concentration in chemotaxis medium for 30 min at 37° C. The chemoattractant, recombinant human IL8 (#Z03262-25, GenScript) was contained in 600 μl chemotaxis medium in each lower chamber at concentration of 10 nM. 250 μl of neutrophil suspension was loaded into each upper chamber and incubated for 60 min at 37° C. After incubation, cells in the chemotaxis media in lower chambers were counted by hemocytometer (#717810, BRAND).

Crystallization, X-Ray Data Collection, and Structure Determination.

Two peptides, pepN48 and pepN9-19, corresponding to residues 1-48 and 9-19 of CXCR2, respectively, were synthesized by Sangon Biotech. The purity and identity of the peptides were tested by HPLC and mass spectrometry. The abN48 Fab was generated by papain (Sigma-Aldrich, at 1:50 w/w ratio) cleavage of abN48-IgG1 (lambda type) at 4° C. overnight in PBS buffer pH 7.4. Following cleavage, abN48 Fab was loaded onto a HiTrap lambda HP column (GE Healthcare) and eluted with 0.1 M sodium acetate at pH 3.0. The elution fractions were pooled and immediately applied to a Superdex200 increase 10/300GL gel filtration column (GE Healthcare) equilibrated with buffer containing 20 mM Tris pH 7.5 and 50 mM NaCl. Fractions containing purified abN48 Fab from the gel filtration column were then pooled and mixed with pepN9-19 (Sangon Biotech) at a molar ratio of 1:3. The mixture was incubated overnight at 4° C. before being further concentrated. The abN48-2 Fab and pepN9-19 complex was assembled following a similar protocol.

Crystals of Fab antibody—peptide complex were obtained at 18° C. using the hanging drop, vapor diffusion method. Diffraction quality crystals of abN48 Fab in complex with pepN9-19 were grown on a siliconized cover clip by mixing 1 μL protein solution (15 mg/mL) with 1 μL reservoir solution (0.1 M HEPES sodium pH 7.5; 2% v/v polyethylene glycol 400; 2.0 M ammonium sulfate). Crystals of abN48-2 Fab in complex with pepN9-19 were obtained in 0.1 M HEPES pH 7.5; 25% w/v polyethylene glycol 3, 350.

The crystals were flash-cooled in liquid nitrogen for data collection after adding 20% glycerol as cryo-protectant. Diffraction data were collected at beamline BL19U1 of the Shanghai Synchrotron Radiation Facility (SSRF) at a wavelength of 0.9789 Å and processed with the HKL3000 program. The structure of abN48 Fab in complex with pepN9-19 was solved by molecular replacement with the Phaser program in PHENIX. The search model was generated by combing a $V_H$ domain built with SWISS-MODEL and a $V_L$ domain from the 4E10 Fab structure (PDBID: 4XCN, chain L). The structure of abN48-2 in complex with pepN9-19 was similarly solved using the abN48-pepN9-19 complex structure as the molecular replacement search model. The initial models were further improved by cycles of manual building and refinement using COOT and Refmac5 in ccp4i. The quality of the final models was analyzed with MolProbity. A summary of the data collection and refinement statistics is outlined in Table S2 Figures were prepared using program PyMol (The PyMOL Molecular Graphics System, Version 2.1 Schrödinger, LLC). Electrostatic calculations were performed with PDB2PQR.

Hydrogen-Deuterium Exchange Mass Spectrometry (HDX-MS)

Amide hydrogen exchange of pepN48 alone was initiated by diluting 1 μL pepN48 at 50 μM into 19 μL $D_2O$ buffer (25 mM Tris, pD 8.0, 150 mM NaCl, 1 mM TCEP) at 10° C. At different time points (0 s, 10 s, 30 s, 60 s and 120 s), the labeling reaction was quenched by the addition of chilled quench buffer (400 mM $KH_2PO_4$/$K_2PO_4$, pH 2.2, 50 mM TCEP) and immediately frozen in liquid nitrogen. For the HDX-MS of pepN48 in the presence of abN48, 1 μL pepN48 at 50 μM was first mixed with 1 μL abN48 at 67 μM. The mixture was then labeled for 0 s, 10 s, 30 s, 60 s or 120 s by adding 18 μL D20 buffer before being quenched and flash-frozen. All frozen samples were stored at −80° C. until analysis.

The thawed samples were immediately injected into HPLC-MS (Agilent 1100) system equipped with in-line peptic digestion and desalting. The desalted digests were then separated with a Hypersil Gold™ analytical column (Thermo) over an 18 min gradient and directly analyzed with an Orbitrap Fusion mass spectrometer (Thermo). The HPLC system was extensively cleaned with blank injections between samples to minimize any carryover. Peptide identification was performed by tandem MS/MS under orbi/orbi mode. All MS/MS spectra were analyzed using the MASCOT program, and final PSMs were filtered with a FDR of 1%. The initial analysis of the peptide centroids was carried out with HD-Examiner v1.3 (Sierra Analytics) and then every peptide was manually verified to check retention time, charge state, m/z range and the presence of overlapping peptides. The peptide coverage of pepN48 was found to be 100% and the relative deuteration levels (% D) of each peptide was automatically calculated by HD-Examiner with the assumption that a fully deuterated sample retains 90% D in current LC setting.

Statistical Analysis

All statistical tests were performed with Graphpad Prism 7 software. Values of measurements were expressed as mean or mean±standard deviation unless otherwise indicated. P value<0.05 was considered significant.

Example 2. Selection of Combinatorial Antibodies that Bind to Human CXCR2

The human CXCR2 protein is a transmembrane protein with an N-terminus and three extra-cellular loops on the outside of the cell. Each of the N-terminus and the three loops has been implicated in the binding of CXCR2 to IL8 (Ahuja, S. K. et al., (1996) *The Journal of biological chemistry* 271, 225-232; Katancik, J. A., et al., (1997) *Biochemical and Biophysical Research Communications* 232, 663-668; Luo, Z. W., et al., (1997) *Protein Engineering* 10, 1039-1045; Berkamp, S., et al., (2017) *Journal of Biomolecular Nmr* 69, 111-121; Park, S. H. et al., (2017) *Biophysical Journal* 113, 2695-2705; Park, S. H. et al., (2011) *JMolBiol* 414, 194-203; and Park, S. H. et al., (2012) *Nature* 491, 779-783).

Through sequence analysis, the instant inventor decided to target the extra-cellular N-terminal 48 amino acids as an epitope in the panning and optimization of highly selective and potent combinatorial antibodies targeting CXCR2 mediated IL8 signaling. A peptide corresponding to the first 48 amino acids of the flexible N terminus of human CXCR2 (pepN48, FIG. 1A) was synthesized (Chinese Peptide, Hangzhou). Three rounds of phage panning using a $10^{11}$ combinatorial library and pepN48 were carried out. Nine scFv sequences showing high enrichment in the panning was sub-cloned into apFuse expression vector. The expression and affinity binding of each scFv combinatorial antibody was confirmed by ELISA screening of the cellular supernatants in the presence of pepN48 peptide (FIG. 5A). Further analysis of the supernatants using FACS showed that, only one clone H8 (abN48), recognized the membrane human CXCR2-mCherry on U20S cells (FIG. 5B). The H8 (abN48) scFv combinatorial antibody was then overexpressed, purified to homogeneity, and subjected to SPR analysis on a Biacore. The $K_D$ value of H8 (abN48) with pepN48 was determined to be $2.6 \times 10^{-9}$ M (FIG. 5C).

Example 3. Generation of Full-Length IgG1 Combinatorial Antibody and Affinity Maturation In order to optimize the binding affinity of H8 (abN48), the scFv antibody was first converted into a full-length combinatorial antibody in IgG1 format (FIG. 6A), and designated as abN48-IgG1. The $K_D$ value of abN48-IgG1 with pepN48 was determined to be $7.8 \times 10^{-10}$ M (FIG. 1B). The improved affinity of abN48-IgG1 comparing to its scFv form suggests the Fab configuration could be further optimized using affinity maturation by yeast display. To maximize the chance in finding the optimal binder(s) for the targeted epitope sequence, all the eleven CDR3 residues on $V_H$ of abN48-IgG1, GYCSSTSCYDY, were randomly mutated, and the resulting Fab sequences were displayed on yeast surface using a pESC vector containing GAL1-10 bi-directional promoter that expresses both heavy and light chains. This generated a combinatorial antibody library of $>10^7$ in volume of diversity. After four rounds of panning against pepN48, 8 highly enriched sequences, abN48-1 to abN48-8, were selected from 100 positive clones and confirmed by sequencing analysis. Weblogo analysis revealed that the most frequent mutations in the enriched sequences are S5R and S7R, which constitute the sequence of a new combinatorial antibody, abN48-2 (FIG. 5B). The 8 sequences were sub-cloned to pFuse vector and expressed by HEK293T cells. Binding affinity and homogeneity of the 8 purified antibodies were determined by SPR and SEC-HPLC, respectively (Table 1 and FIG. 7).

TABLE 1

Kinetic parameters of abN48 and 8 new combinatorial antibodies selected by affinity maturation. Data are displayed using scientific exponential notation.

| | $k_{on}$ (1/Ms) | $ko_{ff}$(1/s) | $K_D$ (M) |
|---|---|---|---|
| abN48 | 3.5E+5 | 3.5E−4 | 7.8E−10 |
| abN48-1 | 2.5E+5 | 6.4E−5 | 2.6E−10 |
| abN48-2 | 9.4E+5 | 1.7E−5 | 7.2E−12 |
| abN48-3 | 3.6E+5 | 1.6E−4 | 6.3E−10 |
| abN48-4 | 5.2E+5 | 1.6E−5 | 3.1E−11 |
| abN48-5 | 8.1E+5 | 1.0E−6 | 1.2E−12 |
| abN48-6 | 8.5E+4 | 1.8E−5 | 2.1E−10 |

TABLE 1-continued

Kinetic parameters of abN48 and 8 new combinatorial antibodies selected by affinity maturation. Data are displayed using scientific exponential notation.

| | $k_{on}$ (1/Ms) | $ko_{ff}$(1/s) | $K_D$ (M) |
|---|---|---|---|
| abN48-7 | 1.3E+7 | 1.5E−4 | 1.2E−11 |
| abN48-8 | 1.2E+6 | 2.0E−5 | 1.6E−11 |

All new constructs showed sub-nanomolar to picomolar binding affinity with pepN48 suggesting a shared common epitope sequence on N-terminus of CXCR2. The combinatorial antibody, abN48-2-IgG1, as shown in FIG. 1B, displayed a pico-molar binding affinity with $K_D$ value of $7.2 \times 10^{-12}$ M, a 100-fold improvement comparing to that of abN48-IgG1. In addition, after incubation at 42° C. for 5 days, abN48-2-IgG1 showed no detectable aggregation or degradation (FIG. 7, top row right).

TABLE 2

Sequences of VH and VL

| Name | Sequence | SEQ ID NO: |
|---|---|---|
| abN48 VH | QVQLVQSGAEVKKPGSSVKVSCKASGGTLS SYAISWVRQAPGQGPEWMGWINPNSGGTNY AQKFQGRVTMTRDTSISTAYMELSRLRPDD TAVYYCASGYCSSTSCYDYWGQGTLVTVSS | 17 |
| abN48-2 VH | QVQLVQSGAEVKKPGSSVKVSCKASGGTLS SYAISWVRQAPGQGPEWMGWINPNSGGTNY AQKFQGRVTMTRDTSISTAYMELSRLRPDD TAVYYCASGYCSRTRCYDYWGQGTLVTVSS | 18 |
| VL for both | QAVLTQPSSLSASPGASVSLTCTLRSGINV GAYRIYWYQQKPGSPPQFLLRYKSDSDKQQ GSGVPSRFSGSRDASANAGILLISGLRSED EADYYCAIWHSSAWVFGGGTQLTVLG | 19 |

The interaction between abN48-IgG1 or ab48-2-IgG1 with pepN48 was further validated and mapped to residues 12-19 and 13-21, respectively using HDX-MS method (FIG. 1C).

Example 4. Combinatorial Antibodies Species and Sub-Type Specifically Bound to hCXCR2

To determine species and sub-type specificities of abN48-IgG1 and abN48-2-IgG1, gene constructs containing hCXCR1-mCherry, hCXCR2-mCherry, mCXCR2-mCherry, rCXCR2-mCherry, rbCXCR2-mCherry, and mcCXCR2-mCherry were overexpressed in U20S cells. Immunofluorescence co-localization of U20S overexpressing hCXCR1-mCherry, hCXCR2-mCherry, mCXCR2-mCherry with abN48-IgG1 and abN48-2-IgG1 showed that both antibodies recognized the surface hICXCR2 specifically (FIG. 2A). This high specificity was further confirmed by FACS analyses, in which both abN48-IgG1 and abN48-2-IgG1 bound exclusively to CXCR2 of human (hCXCR2) and a closer related species macaque monkey (mcCXCR2), but not CXCR1, nor CXCR2 of mouse, rat, or rabbit (FIG. 2B).

Example 5. Combinatorial Antibodies Potently Inhibited hCXCR2 Mediated β-Arrestin Signaling and Calcium Influx To understand cellular functions of the hCXCR2-specific antibody binders, two independent signaling pathways, β-arrestin recruitment and cytoplasmic Ca2+influx, mediated by CXCR2 were evaluated using Tango and FLIPR methods, respectively. β-arrestin recruitment is a G protein-independent intra-cellular event; whereas $Ca^{2+}$influx is a result of $Ca^{2+}$releasing from endoplasmic reticulum (ER) into cytoplasm, responsive to IP3 produced by Ga protein activation, both of which are known to be associated directly with CXCR2 activation.

Natural ligands and two selected combinatorial antibodies were first tested for their agonistic effects in β-arrestin recruitment using Tango assays. Only the two natural ligands, I1L8 and GROα, induced β-arrestin recruitment with apparent $EC_{50}$ values of 4.5 nM and 5.3 nM, respectively (FIG. 3A). The two antibodies, abN48-IgG1 and abN48-2-IgG1, on the other hand, showed no activation of the recruitment up to 100 nM, but complete inhibition of the natural ligand induced recruitment (at $EC_{80}$ level) with apparent IC50 values of 2.8 nM and 0.90 nM, respectively for IL8, and apparent IC50 values of 4.7 nM and 0.37 nM, respectively for GROα (FIG. 3B). It is also noted that both abN48-IgG1 and abN48-2-IgG1 showed inverse agonistic effect, of which both antibodies at 20 nM markedly suppressed the intrinsic β-arrestin recruitment by CXCR2 expression (FIG. 8).

Stimulation of $Ca^{2+}$influx was next examined for IL8, GROα, and the combinatorial antibodies. The natural ligands, I1L8 and GROα, showed dose-dependent activation of $Ca^{2+}$influx with $EC_{50}$ values of 0.42 nM and 1.7 nM, respectively (FIG. 3C). Interestingly, the tight binding antibody, abN48-2-IgG1, displayed a partial agonist effect at high concentration range from 10-1000 nM with an apparent $EC_{50}$ value of 310 nM (FIG. 3C). Both abN48-IgG1 and abN48-2-IgG1, on the other hand, displayed a dose-dependent inhibition of natural ligand induced (at $EC_{90}$ level) $Ca^{2+}$influx with $IC_{50}$ values of 190 nM and 44 nM, respectively for I1L8, and 1000 nM and 110 nM, respectively for GROα (FIG. 3D).

The observed enhancement of antagonist effect on CXCR2 mediated signaling by abN48-2-IgG1 comparing to abN48-IgG1 is consistent with its improved binding affinity with the N-terminal epitope sequences of CXCR2.

Example 6. Combinatorial Antibodies Potently Induced Internalization of hCXCR2

Figure 3E:
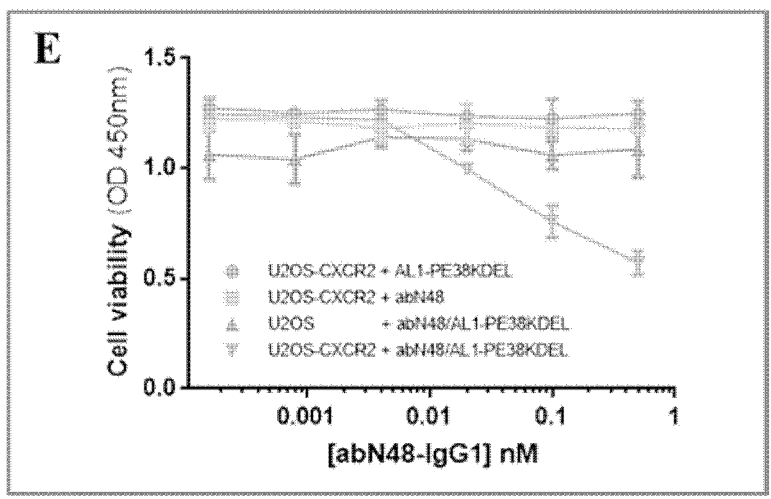

IL8 has also been shown to induce endocytosis signaling of CXCR2 at 5-10 nM. To test the effect of combinatorial antibody ligand on CXCR2 endocytosis, the internalization of CXCR2 was examined using the U20S cells overexpressing membrane hCXCR2 but not FcR receptor. Immunotoxin complex of abN48-IgG1 or abN48-2-IgG1 was used as a molecular probe. As shown in FIG. 3E, only the immunotoxin complexes of abN48-IgG1 and abN48-2-IgG1showed dose-dependent cytotoxicity of U20S overexpressing hCXCR2. The U20S cells without hCXCR2 expression as well as the immunotoxin complex of an irrelevant combinatorial antibody showed no detectable cytotoxicity under the experimental conditions.

The activation effect of abN48-IgG1 or abN48-2-IgG1 was highly sensitive with an apparent $EC_{50}$ value of less than 0.1 nM.

Example 7. Monoclonal Antibody, abN48-2-IgG1, Potently Inhibited IL8-Induced Neutrophil Chemotaxis Neutrophil chemotaxis occurs along the gradient of its corresponding chemokine secreted at a distant acute damage or infectious site. Since CXCR2 is known to express mainly on neutrophils and its cognitive ligand, IL8, has been found a key regulator in many pathological processes, the IL8-CXCR2 axis constitutes an important therapeutic intervention target. This example carried out the chemotaxis study of the optimized combinatorial antibody, abN48-2-IgG1, using primary human neutrophils. Viable Neutrophils were negatively selected via immune-magnetic bead separation from a whole blood collection, and the purity was verified for $CD15^+$, $CD16^+$, $CD11b^+$, $CD66b^+$(MT-Bio, Shanghai).

First, the membrane expression of hCXCR2 on human neutrophils was confirmed by immuno-staining using both abN48-IgG1 and abN48-2-IgG1 (FIG. 4A). FACS analyses showed that the whole population of neutrophil cells could be captured by abN48-IgG1 or abN48-2-IgG1 consistent with previous literature report. Neutrophil chemotaxis by IL8 was next tested in a trans-well migration assay. The combinatorial antibody, abN48-2-IgG1 showed a dose-dependent, highly potent, and complete inhibition of neutrophil chemotaxis induced by maximal IL8 concentration (10 nM) (FIG. 4B). As shown in FIG. 4B, abN48-2-IgG1 showed an extremely potent inhibition of neutrophil chemotaxis with 75% inhibition at 1 nM and 120% inhibition at 20 nM; whereas a small molecule CXCR1/CXCR2 dual inhibitor, MK7123, showed 100% inhibition of neutrophil chemotaxis at 1 μM. The observation of complete blockage of neutrophil migration both chemokine dependent and independent by abN48-2-IgG1 may suggest the involvement of CXCR2 in the basal intrinsic migration of neutrophils.

Example 8. Interaction Between abN48 Antibody and N-Terminus of CXCR2 by Characterized by X-Ray Crystallography and Mutagenesis To identify a minimal interacting peptide sequence of pepN48 for crystallography studies, based on the HDX-MS results (FIG. 1C), this example designed a series of truncates from N—and C-terminus of the pepN48 peptide, and found that a minimum 9-19 amino acid (aa) peptide (pepN9-19, DSFEDFWKGED, SEQ ID NO:16) bound to the Fab forms of both abN48-IgG1 and abN48-2-IgG2 at a level comparable to pepN48, whereas pepN48 lacking 9-19 aa (pepN48Δ9-19) was no longer recognized by the antibodies (FIG. 9).

The crystal structures of abN48 and abN48-2 (Fab form) in complex with pepN9-19 to a final resolution of 2.8 Å (FIG. 1D, Table 3). There are two abN48/pep9-19 protein complexes (protomers) in one asymmetric unit (FIG. 10A). The electron density of bound pepN9-19 in one such protomer (FIG. 10B, left) was much better than in the other (FIG. 10B, right), this example thus focused the analysis on the former one.

TABLE 3

| X-ray data collection and refinement statistics. | |
| --- | --- |
| Data collection | NE |
| Resolution range (Å)* | 39.3-2.80 (2.90-2.80) |
| Space group | C121 |
| Unit cell | 159.5 76.1 85.4 |
| | 90.0 108.5 90.0 |
| Unique reflections* | 24006 (2372) |
| Redundancy* | 6.7 (6.5) |
| Completeness (%)* | 100 (97.0) |
| Mean I/* | 14.2 (1.6) |
| Wilson B-factor (Å$^2$) | 61.4 |
| R-pim (%)* | 4.3 (33.4) |

TABLE 3-continued

X-ray data collection and refinement statistics.

| Data collection | NE |
| --- | --- |
| R-meas (%)* | 11.3 (86.7) |
| CC$_{1/2}$* | 1 (0.750) |
| Refinement statistics | |
| Reflections used in refinement* | 23964 (2372) |
| Reflections used for R-free* | 1168 (118) |
| R-work (%)* | 21.5 (32.0) |
| R-free (%)* | 26.4 (32.9) |
| Protein atoms/solvent atoms | 6452/21 |
| RMSD bond length (Å) | 0.008 |
| RMSD bond angles (°) | 1.26 |
| Ramachandran favored (%) | 97.0 |
| Ramachandran allowed (%) | 99.9 |
| Average B-factor (Å$^2$) | 66.8 |
| protein | 66.8 |
| solvent | 38.8 |

*Statistics for the highest-resolution shell are shown in parentheses.

Notably, in both abN48/pepN9-19 protomers, FW14-15aa of pepN9-19, could be well traced from the electron density (FIG. 10B) indicating that these two residues play key roles in defining the binding between abN48 and pepN9-19. Indeed, the CDR loops of abN48 arranged in such a way that a large hydrophobic cavity forms at the top of its variable region (FIG. 11A and 11B). Residues F14 and W15 insert their bulky aromatic side chains into this hydrophobic cavity, forming strong hydrophobic interaction with residues on all CDR loops except for CDR2L of abN48 (FIG. 11C). Specifically, W104 and F106 in CDR3L, as well as Will in CDR3H of abN48 form strong π-π stacking interactions with W15 from pepN9-19, which also interacts with Y38 in the light chain frame region and W48 in the heavy chain frame region of abN48 (FIG. 11C). Meanwhile, F14 from pepN9-19 forms strong π-π stacking interaction with Y36 in CDR1L, as well as F48 and Y38 in the light chain frame region of abN48 (FIG. 11C). Besides W51 of CDR2H hydrophobically packs against the side chain of K16 from pepN9-19, thereby also contributing to the high affinity interaction between abN48 and NT9-19 (FIG. 11C). Hence, the structure of abN48/NT9-19 undoubtedly indicates that F14 and W15 from the N-terminal region of CXCR2 are the key epitopes that abN48 and abN48-2 recognized. Intriguingly, the CDR2H and CDR3H of abN48 both exist as anti-parallel β-sheets, and CDR3H are even stabilized by a pair of inter α-strands disulfide bonds (C102-C107). Similar conformation of CDR loops has been observed before, albeit quite uncommon.

For further validation, this example carried out alanine-scan site-directed mutagenesis on residues D13, F14, W15, and K16 of N-terminus of hCXCR2. Mutant constructs were fused with mCherry and expressed on U2OS cells which were then checked by FACS and Immunocytofluorescence (FIG. 12). Results were consistent to the crystal analysis that D13, F14 and W15 are the critical epitopes for the binding of antibody ligands. We thus believe that W15 from CXCR2 is highly likely important for the interaction between IL8 and CXCR2 and that abN48 may antagonize CXCR2 by out-competing IL8 in binding F14-W15 of CXCR2.

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference

The invention claimed is:

1. An antibody or fragment thereof, wherein the antibody or fragment thereof has specificity to a human C—X—C Motif Chemokine Receptor 2 (CXCR2) protein and comprises a heavy chain variable region (VH) comprising a CDR1, a CDR2 and a CDR3, and a light chain variable region (VL) comprising a CDR1, a CDR2 and a CDR3, wherein:

the $V_H$ CDR1 comprises the amino acid sequence of SEQ ID NO:1;

the $V_H$ CDR2 comprises the amino acid sequence of SEQ ID NO:2;

the $V_H$ CDR3 comprises the amino acid sequence of SEQ ID NO:3, or a variant selected from the group consisting of SEQ ID NO:7-14;

the VL CDR1 comprises the amino acid sequence of SEQ ID NO:4;

the VL CDR2 comprises the amino acid sequence of SEQ ID NO:5; and the VL CDR3 comprises the amino acid sequence of SEQ ID NO:6.

2. The antibody or fragment thereof of claim 1, wherein the VH CDR3 comprises the amino acid sequence of SEQ ID NO:3.

3. The antibody or fragment thereof of claim 1, further comprising a heavy chain constant region, a light chain constant region, an Fc region, or the combination thereof.

4. The antibody or fragment thereof of claim 1, wherein the antibody is a human antibody.

5. The antibody or fragment thereof of claim 1, wherein the VH comprises the amino acid sequence of SEQ ID NO:17 or 18, or a peptide having at least 90% sequence identity to SEQ ID NO:17 or 18.

6. The antibody or fragment thereof of claim 1, wherein the VH comprises the amino acid sequence of SEQ ID NO:18, or a peptide having at least 90% sequence identity to SEQ ID NO:18.

7. The antibody or fragment thereof of claim 5, wherein the VL comprises the amino acid sequence of SEQ ID NO:19, or a peptide having at least 90% sequence identity to SEQ ID NO:19.

8. One or more polynucleotide encoding the antibody or fragment thereof of claim 1.

9. A method of treating an neutrophil-related inflammatory disease in a patient in need thereof, comprising administering to the patient an effective amount of the antibody or fragment thereof of claim 1.

10. A method of treating cancer in a patient in need thereof, comprising administering to the patient an effective amount of the antibody or fragment thereof of claim 1, wherein the cancer is selected from the group consisting of bladder cancer, liver cancer, colon cancer, rectal cancer, leukemia, lymphoma, pancreatic cancer, small cell lung cancer, non-small cell lung cancer, breast cancer, head and neck cancer, gastrointestinal cancer, stomach cancer, esophageal cancer, ovarian cancer, renal cancer, melanoma, prostate cancer and thyroid cancer.

11. The method of claim 9, wherein the neutrophil-related inflammatory disease is selected from the group consisting of arthritis, rheumatoid arthritis, multiple sclerosis, psoriasis, psoriatic arthritis, Crohn's disease, inflammatory bowel disease, asthma, chronic obstructive pulmonary disease, osteoarthritis ulcerative colitis, lupus, systemic lupus erythematous, juvenile rheumatoid arthritis, juvenile idiopathic arthritis, dermatomyositis, Sjogren syndrome, type I diabetes, and atherosclerosis.

12. The method of claim 9, wherein the neutrophil-related inflammatory disease is caused by an infection.

\* \* \* \* \*